(12) United States Patent
Papot et al.

(10) Patent No.: US 9,000,135 B2
(45) Date of Patent: Apr. 7, 2015

(54) SELF-REACTIVE ARMS AND PRODRUGS COMPRISING SAME

(75) Inventors: Sebastien Papot, Poitiers (FR); Mickael Thomas, Varennes (FR)

(73) Assignees: Centre Nationale de Recherche Scientifique, Paris (FR); Universite de Poitiers, Poitiers (FR)

( * ) Notice: Subject to any disclaimer, the term of this patent is extended or adjusted under 35 U.S.C. 154(b) by 202 days.

(21) Appl. No.: 13/699,173

(22) PCT Filed: May 18, 2011

(86) PCT No.: PCT/IB2011/052184
§ 371 (c)(1),
(2), (4) Date: Jan. 30, 2013

(87) PCT Pub. No.: WO2011/145068
PCT Pub. Date: Nov. 24, 2011

(65) Prior Publication Data
US 2013/0144045 A1 Jun. 6, 2013

(30) Foreign Application Priority Data
May 20, 2010 (FR) ..................................... 10 53921

(51) Int. Cl.
C07C 205/22 (2006.01)
A61K 47/48 (2006.01)
C07D 475/04 (2006.01)
C07H 15/203 (2006.01)
C07H 15/252 (2006.01)

(52) U.S. Cl.
CPC ..... *A61K 47/48023* (2013.01); *A61K 47/48092* (2013.01); *A61K 47/48107* (2013.01); *C07C 205/22* (2013.01); *C07D 475/04* (2013.01); *C07H 15/203* (2013.01); *C07H 15/252* (2013.01)

(58) Field of Classification Search
CPC .................. A61K 47/48092; A61K 47/48107; C07C 205/22
USPC .......................................... 536/17.4; 568/706
See application file for complete search history.

(56) References Cited

U.S. PATENT DOCUMENTS
5,561,119 A 10/1996 Jacquesy et al.

FOREIGN PATENT DOCUMENTS
EP 0 511 917 A1 11/1992
EP 0 642 799 A1 3/1995
EP 2 098 534 A1 9/2009
WO WO 81/01145 4/1981
WO WO 2005/115105 A2 12/2005

OTHER PUBLICATIONS

Gopin et al., "A Chemical Adaptor System Designed to Link a Tumor-Targeting Device with a Prodrug and an Enzymatic Trigger," Angewandte Chemie International Edition, Jan. 2003, vol. 42, pp. 327-332.

Kolb et al., "The growing impact of click chemistry on drug discovery," Drug Discovery Today, Dec. 2003, vol. 8, No. 24, pp. 1128-1137.

Wu et al., "Reaction of Propargyl Bromide with Aldehydes in the Presence of Metallic Tin. Synthesis of Homopropargylalcohols and Homoallenylalcohols," Synthetic Communications, Jan. 1990, vol. 20, No. 9, pp. 1279-1286.

Matsuda et al., "Structure-activity relationships of 1'S-1'-acetoxychavicol acetate for inhibitory effect on NO production in lipopolysaccharide-activated mouse peritoneal macrophages," Bioorganic & Medicinal Chemistry Letters, Apr. 2005, vol. 15, pp. 1949-1953.

Jeffrey et al., "Minor groove binder antibody conjugates employing a water soluble β-glucuronide linker," Bioorganic & Medicinal Chemistry Letters, Jan. 2007, vol. 17, pp. 2278-2280.

Kolb et al., "Click Chemistry: Diverse Chemical Function from a Few Good Reactions," Angewandte Chemie International Edition, 2001, vol. 40, pp. 2004-2021.

Kratz et al., "Prodrug Strategies in Anticancer Chemotherapy," Chem. Med. Chem., 2008, vol. 3, pp. 20-53.

(Continued)

*Primary Examiner* — Brandon Fetterolf
*Assistant Examiner* — Yih-Horng Shiao
(74) *Attorney, Agent, or Firm* — Oliff PLC

(57) ABSTRACT

The present invention relates to a compound of general formula (I):

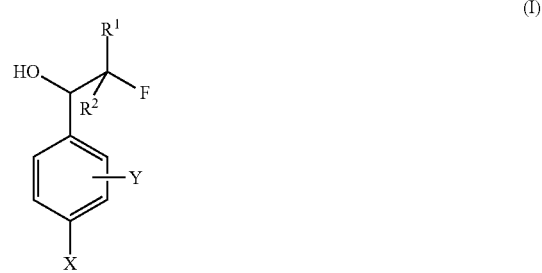

Figure 1:
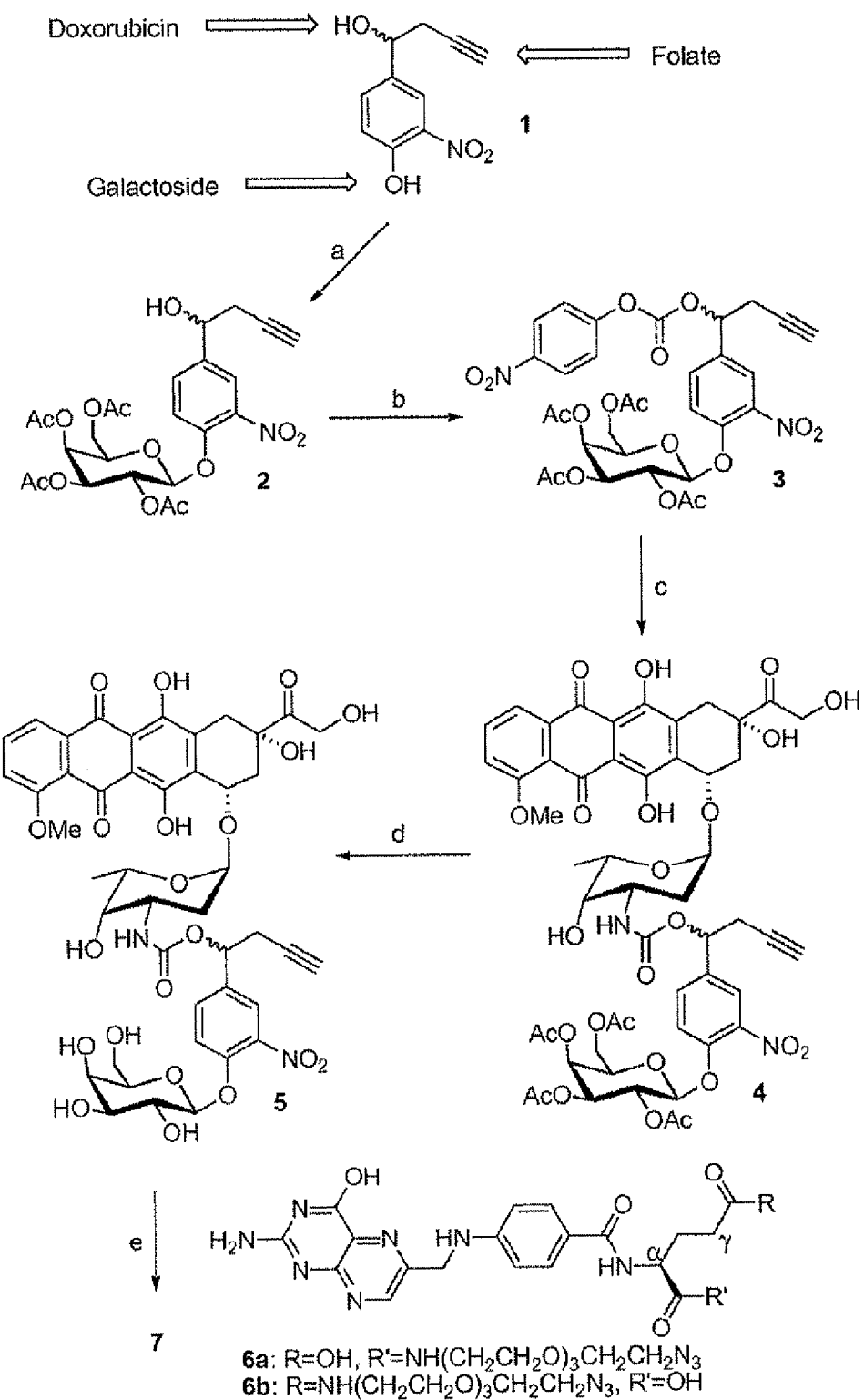

in which:
X is OH, $NH_2$, NHOH or RNH, where R may be a linear or branched, saturated or unsaturated, C1-C10 alkyl radical,
Y is H, or an electron-withdrawing group, in particular selected from $NO_2$, $CF_3$ or a halogen,
R1 and R2 are H or a linear or branched, saturated or unsaturated, C1-C10 alkyl radical,
F is a reactive functional group that can be activated by click chemistry.

26 Claims, 6 Drawing Sheets

(56) References Cited

OTHER PUBLICATIONS

Tranoy-Opalinski et al., "Design of Self-Immolative Linkers for Tumour-Activated Prodrug Therapy," Anti-Cancer Agents in Medicinal Chemistry, 2008, vol. 8, No. 5, pp. 1-20.

Nov. 18, 2010 Written Opinion issued in French Application No. 1053921 (with translation).

Jul. 21, 2011 Written Opinion of the International Searching Authority issued in International Application No. PCT/IB2011/052184.

Jul. 21, 2011 International Search Report issued in International Application No. PCT/IB2011/052184.

SELF-REACTIVE ARMS AND PRODRUGS COMPRISING SAME

The present invention relates to the field of prodrugs and to the preparation thereof. More particularly, the present invention relates to a novel self-immolable or self-reactive arm and its use for the preparation of novel prodrugs. The present invention also relates to novel prodrugs comprising such an arm and suitable for the specific targeting of active compounds in vivo. The present invention further relates to a method for preparing novel prodrugs using a novel self-immolable or self-reactive arm, and to pharmaceutical or diagnostic compositions comprising these prodrugs.

An active compound administered to a living being, for example for a therapeutic or diagnostic purpose, is characterized by an absorption, distribution, metabolization and elimination profile. All the parameters of this profile participate in the definition of its bioavailability and of its therapeutic or diagnostic effects.

According to the characteristics of this profile, an active compound may exert a therapeutic or diagnostic effect in a more or less sustained manner over time, more or less intensely, and may, if applicable, be associated with more or less pronounced side effects. The form in which this active compound is administered may prove to be decisive with regard to its activity profile and its toxicity.

Many active compounds, for example anti-cancer agents, have the drawback of being toxic to healthy tissues or healthy cells, thereby limiting their use.

Cancer is one of the primary causes of death in France today. Among the various feasible methods of treatment, chemotherapy is the only one usable against circulating tumors, such as lymphomas and leukemias, and metastases. However, the anti-cancer agents used clinically have little selectivity toward the tumor cells and also attack the healthy tissues. This nonselective destruction generates severe side effects and, in most cases, leads to the premature interruption of the treatment. The development of novel anti-cancer agents designed to destroy the tumors selectively without affecting the healthy organs therefore represents a major asset in the fight against cancer.

Recent investigations have revealed that tumor tissues could be differentiated from healthy tissues, on the one hand with regard to the tumor microenvironment that is distinguished from the healthy tissues by a more acidic pH, a higher reduction potential, greater peg useability for macromolecules, or else by the presence of a relatively high concentration of certain enzymes, such as β-glucuronidase, and on the other hand, with regard to the malignant cells which overexpress, on their surface, membrane receptors or antigens, such as folic acid receptors or CD33 antigen, which differentiate them from the healthy cells.

In order to reduce the toxicity of active compounds such as anti-cancer agents, or to improve their bioavailability, for example via better solubilization, and their targeting toward target tissues and cells, it has been proposed to vectorize them in the form of prodrugs. These compounds are thus generally made inert by chemical grafting on a molecule intended to convey them, within an organism in which they are administered, up to the target tissues or cells, where they are released.

For this purpose, many molecules having an arm, or spacer, self-immolable or self-reactive function have been proposed to vectorize active compounds in inert form, in a specific and targeted manner.

The self-reactive arm is covalently bonded on the one hand to the active compound to be vectorized, and on the other hand, to a labile group serving to ensure a cellular or tissue specificity and/or an improved solubilization in the biological fluids. The elimination of the labile group leads, by intramolecular rearrangement of the self-reactive arm, to the release of the active compound.

A self-reactive arm must confer sufficient stability on the prodrug to permit its administration, for example orally or systemically, and must therefore be endowed with sufficient reactivity to allow the release of the active compound immediately or virtually immediately after the elimination of the labile group.

Tranoy-Opalinski et al. (Anti-Cancer Agent Med. Chem. 2008(6):2.618-637) described various types of self-reactive arm suitable for preparing prodrugs. In particular, the prodrugs described comprise, as self-reactive arms, a phenol or aniline derivative, leading to a 1,6, elimination, and in which the active compound is attached to a benzyl carbon by means of a carbamate or carbonate function, and the phenol function is bonded to a glucuronyl group eliminable by the action of a β-glucuronidase. The presence of the glucuronide group serves to ensure the tissue specificity of the prodrugs toward the tumors in which β-glucuronidase is strongly expressed.

However, prodrugs whereof the tissue specificity is ensured by a labile group which is a substrate of an enzyme have the drawback of generally requiring that the enzyme ensuring the hydrolysis of this group is previously targeted at the target tissue or organ. Thus, WO 81/01145, EP 0 642 799 or EP 0 511 917 describe the use of such prodrugs in antibody directed enzyme prodrug therapy (ADEPT).

Furthermore, Jeffrey et al. (Bioorg. Med., Chem., Lett., 2007, 17: 2278) describe a prodrug comprising a self-reactive arm derived from phenol on which are grafted a glucuronyl group on the phenol function, an active compound on a benzyl carbon by a carbamate function, and in the ortho position of the phenol function, an antibody by an amido function. The specific direction of the active compound is ensured by the antibody, and the hydrolysis of the glucuronyl group by the action of an intracellular β-glucuronidase ensures the release of the active compound in the target cells. However, the antibodies are macromolecules which do not penetrate the tumor zone very effectively, and are only eliminated very slowly by the organism.

Mention can also be made of Gopin et al, (Angew. Chem. Inter. Ed., 2003, 42: 327) who describe a prodrug comprising an active compound bonded to a self-reactive arm derived from 4-hydroxymandelic acid, on which are fixed, on the one hand, a substrate group of the 38C2 catalyst antibody, and a targeting ligand, HPMA. However, the active compound is only released relatively slowly from this prodrug.

Finally, mention can be made of EP 2 098 534 which describes a prodrug comprising an anthracycline bonded to a self-reactive arm of the para aminobenzylcarbonyl type by a carbamate function on the benzyl carbon, and a glucuronyl group (or glucuronylated trigger) bonded by a carbamate function to the phenyl. The glucuronyl group is furthermore functionalized by a propargyl group which, by click chemistry, allows the fixation of a polyethyleneglycol radical in order to improve the overall hydrosolubility.

The development of prodrugs suitable for vectorizing active compounds in inert form in a stable, specific manner and in large quantities, and of releasing these compounds in a rapid and localized manner, proves to be extremely important for active compounds having a narrow therapeutic window, such as anti-cancer agents for example.

Thus, a need exists for a self-reactive arm suitable for simply and rapidly obtaining prodrugs capable of vectorizing, with very high specificity and in inert form, active compounds having a narrow therapeutic window, in particular anti-cancer agents.

A need exists for a self-reactive arm on which can be grafted, chemically and simply, with high yield, a wide variety of active compounds and groups serving to ensure a tissue and cellular specificity and/or an improved solubilization in biological fluids.

A need further exists for a self-reactive arm allowing the preparation of prodrugs endowed with great stability suitable for administration orally or in the bloodstream and which allow a rapid release, either immediate or quasi-immediate, of the active compound in the tissue or the target cell.

A need further exists for a self-reactive arm suitable for preparing prodrugs serving to direct an active compound, in particular an anti-cancer agent, both at the tissues and at the cells.

A need also exists for novel prodrugs which can simultaneously target the tissue microenvironment and the cells of the target tissue or organ.

A need also exists for prodrugs which can be prepared simply and with a yield suitable for industrial production.

A need further exists for prodrugs endowed with good stability, particularly in the bloodstream, and allowing the immediate or virtually immediate release of the active compound, in particular an anti-cancer agent, in the target tissue under the action of an enzyme or of a change in environmental conditions, such as a change in pH.

A need also exists for novel prodrugs whose targeting parameters, both for the tissue environment and the cells, and the solubility parameters, can be easily and closely modulated.

Finally, a need also exists for a prodrug which can be administered in a quantity compatible with therapeutic or diagnostic use and serving to direct an effective quantity of active compounds in the target tissue(s) or cell(s), It is the object of the present invention to satisfy these needs.

Thus, according to a first aspect, the present invention relates to a compound having the general formula (I):

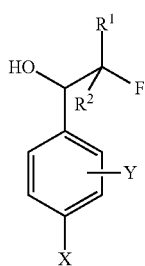

(I)

wherein:
X may be OH, $NH_2$, NHOH or R'NH wherein R' may be a linear or branched, saturated or unsaturated, $C_1$ to $C_{10}$ alkyl radical,
Y may be H or an electron-withdrawing group, in particular selected from $NO_2$, $CF_3$ or a halogen,
$R^1$ and $R^2$, independently of one another, may be H or a linear or branched, saturated or unsaturated, $C_1$ to $C_{10}$ alkyl radical,
F may be a reactive function activable by click chemistry, in particular selected from —C≡CR''', —$N_3$, —SH, —C=$CH_2$, cyclooctynes, maleimide, —$SO_2N_3$, or —COSR''', wherein R''' is H or a linear or branched, saturated or unsaturated, $C_1$ to $C_{10}$ alkyl radical.

Unexpectedly, the inventors found that it was possible, starting with a self-reactive arm derived from phenol, and more particularly of the para-hydroxybenzylcarbonyl type, to introduce a reactive function suitable for click chemistry on the benzyl carbon, in particular a function of the alkyne and particularly ethynyl type, provided that it is bonded to the benzyl carbon, directly or indirectly by means of an spa carbon. The inventors also found that the release kinetics of the active compound could be modulated, and particularly could be accelerated by varying the type of the substituent on one of its ortho or meta positions with regard to the benzyl carbon, and preferably in the meta position.

The inventors have thus developed a novel self-reactive arm on which, by simple chemical reactions, an active compound can be grafted, in particular a therapeutic or diagnostic compound, and in particular an anti-cancer agent, a targeting ligand, in particular a group issuing from a folic acid, and a labile group, in particular by enzyme hydrolysis, in particular a glucuronyl group.

Unexpectedly, a self-reactive arm of the invention can be used advantageously and simply for preparing prodrugs serving to vectorize an active compound, in particular an anti-cancer agent, in an inert manner, and for directing both with regard to the specificities of the tissue environment and with regard to cellular specificities.

The inventors further found unexpectedly that the prodrugs prepared using a self-reactive arm according to the invention were particularly stable in physiological conditions, and that they were capable of releasing an effective quantity of active compounds specifically and very rapidly.

The prodrugs of the invention comprise four distinct units, each designed to exert a particular function.

A first unit consists of an active compound, in particular responsible for therapeutic or diagnostic activity, for example an anti-cancer agent. The active compound is made inert by fixation to the self-reactive arm of the invention, so that its potential toxicity is advantageously masked to avoid affecting the healthy tissues.

A second unit consists of a labile group, in particular enzymatically hydrolyzable, representing a trigger, and which ensures the recognition of a target, particularly an enzyme, selectively localized in the target tissue microenvironment or in a specific type of cells, and whose hydrolysis triggers the release of the active compound.

A third unit consists of the targeting ligand which recognizes a membrane receptor specifically expressed on the surface of the cells of the target tissue and which allows the internalization of the prodrug by the endocytosis mechanism.

Finally, a fourth unit consists of the self-reactive arm of the invention which ensures the cohesion and stability of the prodrug in physiological conditions and the expulsion of the active compound exclusively after elimination of the labile group.

A compound having the general formula (I) according to the invention constitutes a reactive self-reactive arm wherein F, X and —OH on the benzyl carbon are reactive functions which can be mobilized simply and specifically, and on which various compounds can be grafted, in order to form, together with the reactive self-reactive arm of the invention, a prodrug according to the invention.

Thus, according to a second object, the invention relates to a compound having the general formula (II):

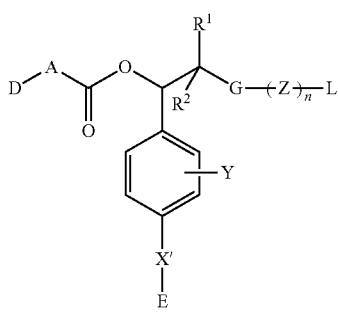

(II)

wherein:
- Y, $R^1$ and $R^2$ are as previously defined,
- X' may be O, NH, NOH, R'N wherein R' is as previously defined,
- E may be a labile group linked to X' by a carboxyl group or an ether bond,
- A may be O, S, NH, NR" wherein R" is a linear or branched, saturated or unsaturated, $C_1$ to $C_{10}$ alkyl group, and preferably may be NH,
- D may be an active compound usable in therapy or diagnosis,
- n=0 or 1, and Z may be a linear or branched, saturated or unsaturated, $C_1$-$C_{10}$ alkylene group optionally interrupted by one or more heteroatoms selected from O or N, a glycosyl group, an O—(CHR$^3$—CHR$^4$—O—)$_m$ or N—(CHR$^3$—CHR$^4$—O—)$_m$ group in which m is a natural integer varying from 1 to 20, $R^3$ and $R^4$, independently of one another, are H or CH$_3$, provided that $R^3$ and $R^4$ are not simultaneously CH$_3$, a group issuing from an amino acid or from a peptide, or a combination thereof,
- L may be a targeting ligand selected from a peptide, a protein, an antibody or an antibody fragment recognizing an antigen, a ligand of a cellular receptor, a biopolymer, a monosaccharide, an oligosaccharide, a hormone, a vitamin, a dendrimer, a polyamine, or a nanoparticle,
- G is a group resulting from a click chemistry reaction between an F group, as previously defined, and an x-(Z)$_n$-L group wherein Z and L are as defined above and x is a reactive function activable by click chemistry and capable of reacting with F, or one of the pharmaceutically acceptable salts thereof.

According to a further object, the present invention relates to a use of a compound having the general formula (I) for preparing a prodrug, in particular represented by compounds having the general formula (II) defined below.

According to a further object, the present invention relates to a method for preparing a compound having the general formula (II) as previously defined, or a pharmaceutically acceptable salt thereof, consisting in reacting a compound having the general formula (I) as previously defined with D-v, E-w, and L-(Z)$_n$-x groups, wherein D, E and L can be as previously defined, and v, w and x are each a reactive function such that, with regard to the compound having the general formula (I), v reacts with OH linked to the benzyl carbon, or said previously activated OH, w reacts with X, and x reacts with F.

The reactive functions v, w and x may be naturally present on the D, E and L-(Z)$_n$ groups, or may, prior to the reaction step, be introduced on the D, E and L-(Z)$_n$ groups.

According to a further object, the present invention relates to a compound, or a pharmaceutically acceptable salt thereof, which can be obtained by a method of the invention.

According to a further aspect, the invention relates to a pharmaceutical or diagnostic composition comprising at least an effective quantity of at least one compound having the general formula (II) according to the invention, or a pharmaceutically acceptable salt thereof.

According to a further object, the present invention relates to a kit for preparing a compound having the general formula (II) as previously defined, or a pharmaceutically acceptable salt thereof, comprising at least one compound having the general formula (I) as previously defined, and at least one group selected from D-v, E-w and L-x, in which L, D and E are as previously defined and v, w and x are as previously defined.

According to one embodiment, a kit of the invention may further comprise at least one instruction for using the compound having the general formulas (I) with said group selected from D-v, E-w and L-x.

In the context of the invention, "self-reactive arm" means a compound capable of releasing, by intramolecular rearrangement, groups previously grafted thereon.

In the context of the invention, "prodrug" means a molecule capable of conveying an active compound in inert form within an organism, and of releasing same into an organ, a tissue or specifically targeted cells under the action, for example, of a specific enzyme or of particular pH conditions.

A self-reactive arm according to the invention may advantageously serve to simply and specifically fix an active compound and two groups intended for targeting the active compound and/or improving its solubility in a biological environment.

According to another advantage, a self-reactive arm according to the invention is endowed with reactive functions serving to obtain prodrugs simply and in large quantities.

According to another advantage, a self-reactive arm according to the invention allows the preparation of stable prodrugs, capable of conveying an active compound in inert form, endowed with a dual tissue and cellular specificity, and suitable for releasing said active compound effectively and rapidly, in a targeted manner.

According to a further advantage, the present invention serves to have prodrugs, suitable for use in diagnosis or therapy, and allowing the targeted transport of an active compound in inert form, and its direction specifically both with regard to the tissue microenvironment and with regard to receptors or proteins present on the surface of the target cells.

According to a further advantage, the present invention serves to have stable prodrugs, endowed with a dual tissue and cellular specificity, and activable within specifically targeted cells.

According to a further advantage, the present invention serves to have prodrugs which are stable and activable in the tissue environment of the target tissue by means of specific enzymes present in said tissue or previously directed by coupling with an antibody.

According to a further advantage, the present invention serves to have prodrugs whose solubility can be easily controlled and improved, According to a further advantage, a self-reactive arm of the invention is particularly suitable for preparing prodrugs intended for vectorizing anti-cancer compounds.

Self-Reactive Arm

A self-reactive arm according to the invention can be illustrated by the following general formula (I):

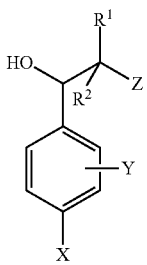

(I)

wherein:
- X may be OH, $NH_2$, NHOH or R'NH wherein R' may be a linear or branched, saturated or unsaturated, $C_1$ to $C_{10}$ alkyl radical,
- Y may be H or an electron-withdrawing group, in particular selected from $NO_2$, $CF_3$ or a halogen,
- $R^1$ and $R^2$, independently of one another, may be H or a linear or branched, saturated or unsaturated, $C_1$ to $C_{10}$ alkyl radical,
- F may be a reactive function activable by click chemistry.

According to a preferred embodiment, X may be OH, $NH_2$, NH(OH) or R'NH wherein R' may be a linear or branched, saturated or unsaturated, $C_2$ to $C_8$, preferably $C_3$ or $C_6$, and preferably $C_4$ or $C_5$, alkyl radical. Even more preferably, R' may be a $C_1$, $C_2$ or $C_3$ alkyl radical.

Even more preferably, X may be OH.

In particular, Y may be an electron-withdrawing group selected from $NO_2$, $CF_3$ or a halogen.

According to an embodiment, Y may represent $NO_2$, a halogen selected from Cl or Br, or $CF_3$. In particular, Y may represent $NO_2$ or Cl, and may preferably be $NO_2$.

Preferably, Y may be in the ortho position of X.

According to an even more preferred alternative embodiment, Y may represent $NO_2$ in the ortho position with regard to X.

According to an embodiment, $R^1$ and $R^2$, independently of one another, may be H or a linear or branched, saturated or unsaturated, $C_1$ to $C_{10}$, preferably $C_2$ to $C_8$, preferably $C_3$ or $C_6$, and preferably $C_4$ or $C_5$, alkyl radical. Even more preferably, $R^1$ or $R^2$ may be a $C_1$, $C_2$ or $C_3$ alkyl radical.

According to an alternative embodiment, $R^1$ may be an alkyl group, in particular a methyl, an ethyl or a propyl, and $R^2$ may be H. According to another embodiment, $R^1$ may be H and $R^2$ may be an alkyl group, in particular a methyl, an ethyl or a propyl.

According to a preferred alternative embodiment, $R^1$ and $R^2$ each represent H.

F is a reactive function activable by click chemistry. Click chemistry is a reaction process known to a person skilled in the art. In this respect, reference can be made to the review of Kolb et al. (Angew. Chem. Int. Ed., 2001, 40: 2004).

According to an embodiment, F is a reactive function activable by click chemistry selected from F representing —C≡CR''', —$N_3$, —SH, C═$CH_2$, cyclooctynes, maleimide, —$SO_2N_3$, or —COSR''', wherein R''' is H or a linear or branched, saturated or unsaturated, $C_1$ to $C_{10}$ alkyl radical.

According to a preferred embodiment, F is a reactive function activable by click chemistry selected from —C≡CH, —$N_3$, —SH, —C═$CH_2$, cyclooctynes, maleimide, —$SO_2N_3$, or COSR.

According to a particularly preferred embodiment, a self-reactive arm suitable for the invention may have the following formula (Ia):

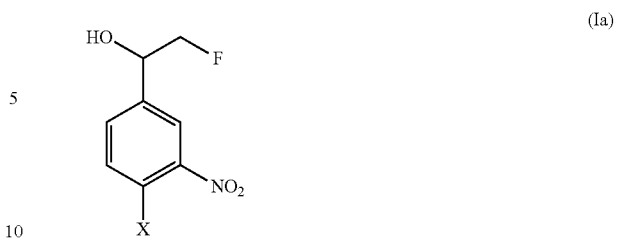

(Ia)

wherein X and F are as previously defined.

Even more preferably, a self-reactive arm suitable for the invention may have the formula (Ia) wherein X is OH and F is as previously defined.

According to another particularly preferred embodiment, a self-reactive arm suitable for the invention may have the following formula (Ib):

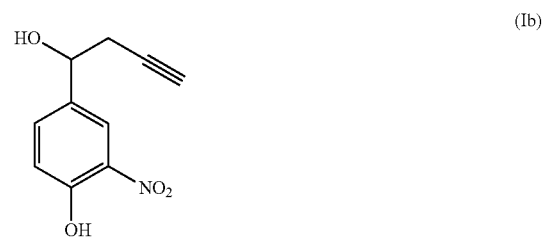

(Ib)

A self-reactive arm suitable for the invention may, for example, be obtained from 4-hydroxy-3-nitrobenzaldehyde or 4-aminobenzaldehyde caused to react in an appropriate solvent and in the presence of optional catalyst(s) with any reagent suitable for introducing a reactive function on the benzyl carbon that is suitable for carrying out subsequent reactions by click chemistry.

According to a particular embodiment, a self-reactive arm according to the invention comprising, as a reactive function F, a —C≡CH group and, as an X group, an OH function, can be obtained by a method comprising a step of reacting 4-hydroxy-3-nitrobenzaldehyde with organo-aluminum propargyl bromide, in an appropriate solvent.

A solvent suitable for such a method may, for example, be tetrahydrofuran.

Such a method may be carried out in the presence of catalysts. A suitable catalyst for the invention may, for example, be mercuric chloride ($HgCl_2$).

According to an alternative embodiment, such a method may comprise a step of heating, for example under reflux, 4-hydroxy-3-nitrobenzaldehyde in the presence of the catalyst, in particular mercuric chloride ($HgCl_2$).

According to an alternative embodiment, such a method may comprise a step of hydrolyzing the product obtained after reaction of 4-hydroxy-3-nitrobenzaldehyde with propargyl bromide in the presence of HCl.

A method according to the invention may further comprise a step consisting in isolating and/or purifying the product obtained. The isolating and/or purifying steps may be carried out by any technique known to a person skilled in the art.

Prodrugs

A prodrug according to the invention may have the following general formula (II):

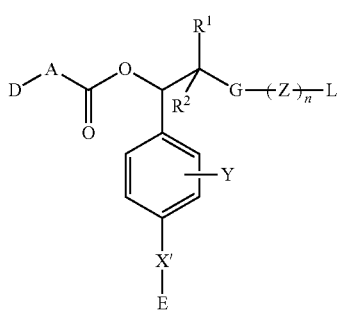

(II)

wherein:
- Y, $R^1$ and $R^2$ are as previously defined,
- X' may be O, NH, NOH, R'N wherein R' is as previously defined,
- E may be a labile group linked to X' by a carboxyl group or an ether bond,
- A may be O, S, NH, NR" wherein R" is a linear or branched, saturated or unsaturated, $C_1$ to $C_{10}$ alkyl group, and preferably may be NH,
- D may be an active compound usable in therapy or diagnosis,
- n=0 or 1, and Z may be a linear or branched, saturated or unsaturated, $C_1$-$C_{10}$ alkylene group optionally interrupted by one or more heteroatoms selected from O or N, a glycosyl group, an O—(CHR³—CHR⁴—O—)$_m$ or N—(CHR³—CHR⁴—O—)$_m$ group in which m is a natural integer varying from 1 to 20, $R^3$ and $R^4$, independently of one another, are H or $CH_3$, provided that $R^3$ and $R^4$ are not simultaneously $CH_3$, a group issuing from an amino acid or from a peptide, or a combination thereof,
- L may be a targeting ligand selected from a peptide, a protein, an antibody or an antibody fragment recognizing an antigen, a ligand of a cellular receptor, a biopolymer, monosaccharide, an oligosaccharide, a hormone, a vitamin, a dendrimer, a polyamine, or a nanoparticle,
- G is a group resulting from a click chemistry reaction between an F group, as previously defined, and an x-(Z)$_n$-L group wherein Z and L are as defined above and x is a reactive function activable by click chemistry and capable of reacting with F, or a pharmaceutically acceptable salt thereof.

According to a preferred embodiment, a prodrug of the invention may have the general formula (II), wherein Y may be $NO_2$ in the ortho position of V, and $R^1$ and $R^2$ may be H.

A pharmaceutically acceptable salt of a compound having the general formula (II) according to the invention may be a salt of a compound having the general formula (II) and of an alkali metal, an alkaline earth metal, or a ammonium, comprising the salts obtained with organic ammonium bases, or salts of a compound having the general formula (II) and of organic or inorganic acid.

Salts more particularly suitable for the invention may be salts of sodium, potassium, calcium, magnesium, quaternary ammonium salts such as tetramethylarnmonium or tetraethylammonium, and addition salts with ammonia and pharmaceutically acceptable organic amines, such as methylamine, dimethylamine, trimethylamine, ethylarnine, triethylamine, ethanolamine and tris(2-hydroxyethyl)amine.

Salts of a compound having the general formula (II) and of inorganic acid suitable for the invention may be obtained with hydrochloric acid, hydrobromic acid, sulfuric acid, nitric acid or phosphoric acid.

Salts of a compound having the general formula (II) and of organic acid suitable for the invention may be obtained with carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, rnethanesulfonic acid, benzenesulfonic acid or p-toluenesulfonic acid.

The prodrugs according to the invention are particularly suitable for the treatment and/or prevention of diseases or disorders involving the overexpression or release of intracellular enzymes which can cleave the labile group E.

As diseases which can be considered by the invention, mention can be made in particular of cancers, auto-immune or inflammatory diseases, immunological or metabolic diseases, or arthropathies.

Preferably, the prodrugs of the invention are suitable in particular for the treatment and/or prevention of cancers, inflammatory diseases, and arthropathies.

Even more preferably, the prodrugs of the invention are suitable in particular for the treatment and/or prevention of a cancer selected from lung cancer, breast cancer, colon cancer, kidney cancer, brain tumors, and leukemias.

According to an embodiment, the invention relates to a pharmaceutical or diagnostic composition comprising at least an effective quantity of at least one compound having the general formula (II) as previously defined, or a pharmaceutically acceptable salt thereof.

A composition according to the invention may comprise at least one pharmaceutically acceptable excipient, such as additives, binders, swelling or lubricating agents, or solubilization agents usually employed in the field.

As a pharmaceutically acceptable excipient suitable for the invention, mention can be made of magnesium carbonate, titanium dioxide, lactose, mannitol and other sugars, talc, lactoproteins, gelatin, starch, cellulose and derivatives thereof, animal or vegetable oils, such as cod liver oil, sunflower, walnut or sesame oil, polyethylene glycol, and solvents such as water and mono- or polyalcohols such as glycerol.

If applicable, a composition of the invention may comprise other appropriate active compounds.

A composition according to the invention may be formulated in any appropriate galenic form such as an injectable solution, tablets, capsules, or transdermal patches.

The choice of the galenic form and of the pharmaceutically acceptable excipients to be used, and if applicable of other active compounds, depends in particular on the method of administration considered and the pathology to be treated or to be prevented, and pertains to the general knowledge and the usual practice of a person skilled in the art.

In the context of the invention, "effective quantity" means the quantity necessary and sufficient to obtain the desired effect according to the invention, that is to say, the pharmacological, therapeutic or diagnostic activity of the active compound D after administration of a prodrug according to the invention. According to a preferred embodiment, a desired pharmacological effect may be an effect of prevention and/or treatment with regard to a cancer.

An effective quantity depends on the type of active compound D, the desired pharmacological effect, the individual to whom a prodrug of the invention is administered, and his physiopathological condition.

An effective quantity may easily be determined by any method known to a person skilled in the art, in particular, for example, by means of clinical trials.

In the context of the invention, "prevention" or "prevent" with regard to a disease, and particularly cancer, means the fact of reducing the risk of occurrence of this disease.

According to an embodiment, a pharmaceutical composition of the invention may comprise a compound having the general formula (II) or a pharmaceutically acceptable salt thereof; wherein the active compound D is an anti-cancer agent, in particular as defined below, and the composition is intended for the prevention and/or treatment of a cancer.

Active Compound D

An active compound D suitable for the invention may be selected from compounds having therapeutic activity and/or diagnostic activity.

More particularly, an active compound D according to the invention may be selected from compounds that are therapeutically active to diseases of the gastro-intestinal tract, diseases of the cardiovascular system, diseases of the central nervous system, pain, mood disorders, diseases of the ophthalmic system, diseases of the oropharyngeal tract, diseases of the respiratory tract, diseases of endocrine secretions and of the metabolism, diseases of the reproductive and urinary system, viral, bacterial or parasitic infections, diseases of the immune system, allergic diseases, cancers, or agents in obstetrics and gynecology, of the skin, or selected from compounds for contraceptive purposes.

According to an embodiment, an active compound D according to the invention may be selected from hormones, agonists or antagonists of a hormone, such as progesterone, busereline, tamoxifen, mifepristone or onapristone, from anti-inflammatories, such as non-steroidal anti-inflammatories, steroidal compounds, analgesics, antipyretics, local anesthetics, anti-arrhythmics, such as antagonists of calcium channels, antihistaminics, sympathomimetics, urokinase inhibitors, antidepressants, antihypertensives, anti-cancer agents, compounds reducing cellular resistance to cytostatics, such as calmodulin inhibitors, protein kinase C inhibitors, glycoprotein-P inhibitors, hexokinase modulators linked to mitochondrias, inhibitors of g-glutamylcysteine synthetase or glutathione-S-transferase, inhibitors of superoxide dismutase, or from immunosuppressant compounds, such as macrolides, cyclosporine A, rapamycin, FK 506, azothioprine, methotrexate, cyclophosphamide or chlorambucil.

Even more particularly, an active compound D according to the invention may be an anti-cancer agent selected from cytostatics, antimetabolites, DNA intercalating substances, topoisomerase I and II inhibitors, tubulin inhibitors, alkylating agents, neocarzinostatin, calicheamycin, dynemicin or esperamycin A, ribosome inhibitors, tyrosine phosphokinase inhibitors, compounds inducing cellular differentiation, or histone deacetylase inhibitors.

Even more particularly, an active compound D according to the invention may be an anti-cancer agent selected from cytostatics and antimetabolites, such as 5-fluorouracil, 5-fluorocytidine, 5-fluorouridine, cytosine arabinoside or methotrexate, from DNA intercalating substances such as doxorubicin, daunomycin, idarubicin, epirubicin or mitoxantrone, from topoisomerase I and II inhibitors, such as camptothecin, etoposide or m-AMSA, from tubulin inhibitors, such as vincristine, vinblastine, vindesine, taxol, nocodazole or colchicin, from alkylating agents, such as cyclophosphamide, mitomycin C, rachelmycin, cisplatin, mustard gas phosphoramide, melphalan, bleomycin, N-bis(2-chloroethyl)-4-hydroxyaniline, or from neocarzinostatin, calicheamicin, dynemicin or esperamycin A, or from ribosome inhibitors, such as verrucarin A, from tyrosine phosphokinase inhibitors, such as quercetin, genistein, erbstatin, tyrphostin or rohitukin and derivatives thereof, from compounds inducing cellular differentiation, such as retinoic acid, butyric acid, phorbol esters or aclacinomycin, from histone deacetylase inhibitors, such as CI-994 or MS275.

According to a particularly preferred embodiment of the invention, an active compound D suitable for the invention may be selected from CI-994 and doxorubicin, and MS275.

According to another embodiment, an active compound D suitable for the invention may be a diagnostic compound, selected in particular from radioligands.

A radioligand suitable for the invention may be a compound carrying a radioactive group, in particular selected from $^3H$, $^{14}C$, $^{35}S$, $^{131}I$, $^{125}I$ or $^{18}F$.

According to an embodiment, D may consist of an active compound or alternatively of a plurality of active compounds. Advantageously, when D consists of a plurality of active compounds, they are interrelated by a self-immolable chemical amplifier. When a plurality of active compounds are present, they may be identical or different.

An amplifier suitable for the invention comprises a plurality of reactive functions, and preferably at least three reactive functions, in order to permit its bonding to a reactive arm of the invention and to at least two active compounds. It is further endowed with the capacity to undergo spontaneous decomposition which is for the release of the active compounds, after its release from a reactive arm of the invention. Even more preferably, a self-immolable amplifier suitable for the invention may comprise at least three, or even at least four reactive functions.

As an example of an amplifier suitable for the invention, mention can be made of 2,4-bis(hydroxymethyl)aniline, 2,4,6-ter(hydroxymethyl)aniline, 2,4 bis(hydroxy-methyl)phenol, or 2,4,6-ter(hydroxymethyl)phenol. These self-immolable amplifiers are linked to the reactive arm of the invention via the phenol or aniline function.

Preferably, a self-immolable function suitable for the invention may be 2,4-bis(hydroxymethyl)aniline.

According to a further embodiment, an amplifier suitable for the invention may comprise a sequence of at least two, or even three, or even four self-immolable amplifying units such as defined above. Each self-immolable amplifying unit of such a sequence is linked to at least one other self-immolable amplifying unit and to at least one active compound. The active compounds are released in a cascade, following the spontaneous decomposition of each amplifying unit, also released in a cascade, following the release of the unit linked to the reactive arm of the invention.

An amplifier of the invention may have the following general formula (III):

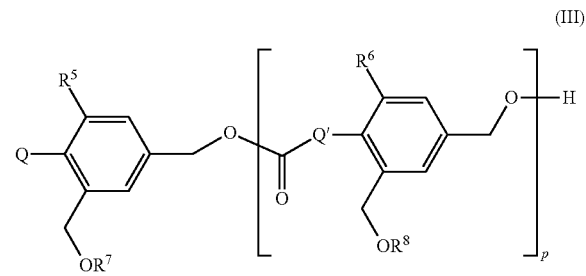

wherein
p may be a natural integer varying from 0 to 3, and preferably from 1 to 2. Even more preferably, p is 0, 1 or 2.

Q may be —NH$_2$ or —OH, and is preferably —NH$_2$, each Q', independently of one another, may be NH or O, and is preferably NH, R$^5$ and R$^6$, independently of one another, may be H or —CH$_2$OR$^9$, wherein R$^9$ may be R$^7$ or R$^8$ as defined below, —R$^7$ and R$^8$, independently of one another, may be H or a subunit having the following general formula (IV):

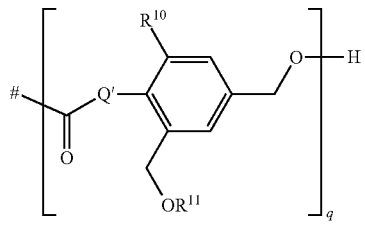

where:

# represents a bond with a benzyl oxygen, q may be a natural integer varying from 0 to 3, and preferably from 1 to 2. Even more preferably, q is 0, 1 or 2, Q' is as defined above, R$^{10}$ may be R$^5$ or R$^6$ as defined above, and R$^{11}$ may be R$^7$ or R$^8$ as defined above.

Preferably, at least one of R$^5$ and of R$^6$ may be H and at least one of R$^5$ or of R$^6$ may be —CH$_2$OR$^9$, wherein R$^9$ is as defined above.

Preferably, at least one of R$^7$ or of R$^8$ may be H and at least one of R$^7$ or of R$^8$ may be a subunit having the general formula (IV) as defined above.

Advantageously, a self-immolable amplifier suitable for the invention defines a dendrimeric structure with at least two, or even 3, or 4 generations.

According to an embodiment, D, in a compound having the general formula (II) as defined above, may represent a compound having the general formula (V):

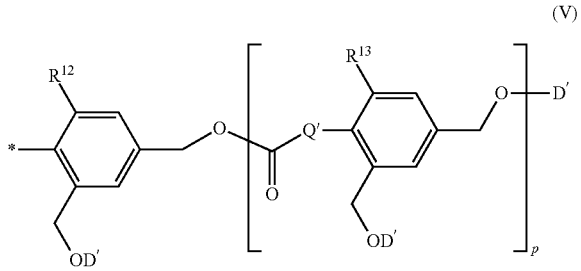

wherein

Q' and p are as defined above,

* represents a bond with A as defined with regard to the general formula (II),

R$^{12}$ and R$^{13}$ may, independently of one another, be H or —CH$_2$OD', where D' is as defined below, and D' may represent an active compound as defined above, or a subunit having the following general formula (VI):

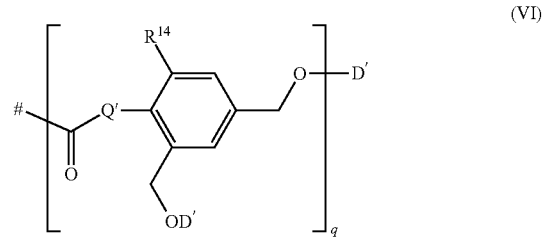

wherein

, Q', D', and q are as defined above,

R$^{14}$ may be H or —CH$_2$OD', where D' is as defined above.

Advantageously, a compound D of the invention may have a dendrimeric structure with at least two, or even three or four generations.

Labile Group E

According to an embodiment, a labile group E suitable for the invention may in particular be an enzymatically hydrolyzable substrate.

A labile group E suitable for the invention is such that its elimination, for example by enzymatic method or subsequent to a pH variation, ensures a release of the active compound D by intra-molecular rearrangement of the self-reactive arm.

A labile group E according to the invention, in particular enzymatically hydrolyzable, may be more particularly selected to confer a tissue and/or cellular specificity to the prodrugs according to the invention.

According to a preferred embodiment, a labile group E suitable for the invention may be enzymatically hydrolyzable.

According to an embodiment, an enzymatically hydrolyzable labile group E according to the invention may be selected so as to be hydrolyzed by one or more enzymes whose expression is specifically attached to a target tissue or target cells.

Among the enzymes suitable for the invention, mention can be made in particular of carboxylesterases, alkaline phosphatases, glucuronidases, and particularly β-glucuronidase, glycosidases, proteases, peptidases, or metalloproteases.

The selection of a labile group E that is an appropriate substrate of an enzyme belonging to the group defined above pertains to the general knowledge of a person skilled in the art.

According to a preferred embodiment, a labile group E may be a substrate of an enzyme selected from glucuronidases, and in particular β-glucuronidase, glycosidases, proteases, peptidases, and metalloproteases.

According to a preferred alternative embodiment, an enzymatically hydrolyzable labile group E suitable for the invention may be a substrate selected from the substrates of galactosidase, and in particular β-galactosidase, induronidase, glucosidase, N-acetyl-D-glucosaminidase, N-acetyl-D-galactosaminidase, mannosidase, fucosidase or glucuronidase, in particular β-glucuronidase, the substrates of cathepsins, or substrates of metalloproteases, in particular PSMA (Prostate Specific Membrane Antigen), According to an even more preferred alternative of the invention, an enzymatically hydrolyzable labile group E suitable for the invention may be a substrate of an enzyme selected from β-glucuronidase, β-galactosidase, cathepsins, or metalloproteases, and in particular PSMA.

According to an embodiment, an enzymatically hydrolyzable labile group E suitable for the invention may in particular be selected from a glycosyl group or a peptide group.

According to an alternative embodiment, an enzymatically hydrolyzable labile group E suitable for the invention may in particular be selected from a glycosyl group, in particular a D-glucuronyl group, an L-iduronyl group, a D-glucopyranosyl group, a D-galactopyranosyl group, an N-acetyl-D-glucosaminyl group, an N-acetyl-D-galactosaminyl group, a D-mannopyranosyl group, an L-fucopyranosyl group.

According to another alternative embodiment, an enzymatically hydrolyzable labile group E suitable for the invention may in particular be a polysaccharide comprising 2 to 20, in particular 3 to 10, and more particularly 4 to 6 ase units selected from the osidic groups defined above.

According to another preferred alternative embodiment, an enzymatically hydrolyzable labile group E suitable for the invention may be a group selected from a D-glucuronyl group, a D-galactopyranosyl group, a D-glucopyranosyl group, or a mannopyranosyl group.

Even more preferably, an enzymatically hydrolyzable labile group E suitable for the invention may be a D-glucuronyl group.

β-Glucuronidase is an enzyme naturally present in a high concentration in the neighborhood of many tumors. The prodrugs of the invention comprising a glucuronyl group as a labile group E can therefore be advantageously activated at the extracellular level, in the course of the Prodrug Mono-Therapy (PMT). Furthermore, β-glucuronidase and β-galactosidase are two lysosomal enzymes which are present in most malignant cells. Thus, the activation of the glucuronylated or galactosylated prodrugs by the corresponding enzymes can be carried out in the intracellular medium after their internalization by endocytosis.

According to another embodiment, an enzymatically hydrolyzable labile group E may be a substrate of a protease or a peptidase, in particular a substrate of a cathepsin or of a metalloprotease, in particular PSMA.

According to another embodiment, the tissue and/or cellular specificity by an enzymatically hydrolyzable labile group E can be provided after directing the enzyme suitable for hydrolyzing the group E at the target tissues or cells, for example by means of an antibody.

In this embodiment, the enzyme is previously fixed to a specific antibody of the targeted tissues or cells, and the conjugate thus obtained is administered prior to the administration of a prodrug of the invention.

This type of method is known to a person skilled in the art, and is called Antibody Directed Enzyme Prodrug Therapy (ADEPT).

It pertains to the skill of a person skilled in the art to select the type of group X of a self-reactive arm according to the invention represented by the general formula (I) or (Ia) as a function of the enzymatic reaction, and hence of the enzyme, which must lead to the elimination of the labile group E.

In the case of esterases, X is selected so that E and X' together form an ester or carbonate function.

In the case of glycosidases, X is selected so that E and X' together form a glycosidic bond.

In the case of peptidases and proteases, X is selected so that E and X' together form an amide function.

According to an embodiment, when the labile group E is a glycosyl group, for example a D-galactopyranosyl group or a D-glucuronyl group, X may preferably be an OH group.

Thus, according to a preferred embodiment, a compound having the general formula (II) suitable for the invention may be such that X' is O and E is a glycosyl group, preferably selected from a D-galactopyranosyl group, a D-glucuronyl group, a D-glucopyranosyl group, or a mannopyranosyl group.

According to another embodiment, when the labile group E is of the peptide or protein type, X may preferably be an $NH_2$ group.

Thus, according to an embodiment, a compound having the general formula (II) suitable for the invention may be such that X' is NH and E is a peptide group which is a cathepsin or protease substrate, and in particular a cathepsin substrate, such as Ala-Leu-Ala-Leu.

According to another preferred embodiment, E may be a peptide group which is a PSMA substrate.

Targeting Ligand L

A targeting ligand suitable for the invention serves advantageously to direct a prodrug of the invention to an organ, a tissue or specific cells.

More particularly, a targeting ligand L suitable for the invention serves advantageously to direct a prodrug of the invention to a tumor or to malignant cells.

According to an embodiment, a targeting ligand L may further comprise a group Z intended to modulate the solubility, and in particular to improve the solubility in the biological fluids, of a prodrug of the invention.

According to an embodiment, a targeting ligand suitable for the invention may have the form $L\text{-}(Z)_n$— wherein n may be equal to 0 or 1, and L and Z are in particular as defined below.

A targeting ligand L may be selected from a peptide, a protein, an antibody or an antibody fragment recognizing an antigen, a ligand of a cellular receptor, a biopolymer, a monosaccharide, an oligosaccharide, a hormone, a vitamin, a dendrimer, a polyamine, or a nanoparticle, metallic or not.

A targeting ligand L suitable for the invention may be selected from ligands suitable, for example, for targeting integrins, nucleolin, N-aminopeptidase, endoglin, the vascular epithelial growth factor receptor, low density lipoprotein (LDL) receptors, transferrin receptors, somatostatin receptors, bombesin, Neuropeptide Y, luteinizing hormone release hormone receptor, folic acid receptors, epidermal growth factor (EGF) receptors, transforming growth factor (TGF) receptors, fibroblast growth factor (FGF) receptors, asialoglycoprotein receptors, galectin receptors, selectin receptors, or hyaluronic acid receptors.

A targeting ligand L suitable for the invention may in particular be a ligand described by Kratz et al. (Chem. Med. Chem., 2008, 3:20).

"Biopolymer" means a biocompatible polymer. A biopolymer suitable for the invention may be an N-(2-hydroxypropyl)methacrylamide copolymer. Such a polymer can ensure the targeting of a prodrug of the invention toward the tumors by the enhanced permeability and retention effect (EPR), associated with the specific vascularization of the tumors.

A monosaccharide suitable for the invention may for example be glucose, galactose, or mannose.

An oligosaccharide suitable for the invention may for example be lactose.

A peptide suitable for the invention may for example be an RGD peptide, peptides bonding to the artery walls, a peptide issuing from EGF, or a peptide issuing from NGF.

A protein suitable for the invention may for example be a lectin, such as concanaline A or mannan-binding lectin, a selectin, a galectin, a growth factor, such as VEGF, FGF or NGF, proteins of surfactant A and B, asialoglycoproteins, malaria circumsporozoite proteins, or Rap protein.

An antibody or an antibody fragment recognizing an antigen suitable for the invention may for example be an anti-CD3 antibody, an anti-CD5 antibody, an anti-CD117 antibody, an anti-ErbB2 antibody, an IgG, an anti-HER2 antibody, a ChCE7 antibody, an OV-TL16 Fab' antibody, an anti-PECAM antibody, an anti-thrombomodulin antibody, or an anti-Tn antibody, an anti-CD20 antibody, an anti-CD33 antibody, an anti-CEA antibody, an anti-glycoprotein antibody of the mucin type (MUC-1, CanAg, Lewis Y, Lewis X), an anti-CT7 antibody, an anti-MAGE antibody, or an anti-PSMA antibody.

A ligand of a cellular receptor suitable for the invention may for example be folic acid, Neuropeptide Y, leptin, an EGF, FGF, TOP, or NGF receptor ligand, insulin, a synthetic mannosylated ligand, transferrin or a catecholamine.

A hormone suitable for the invention may for example be progesterone, an estrogen, testosterone, anti-diuretic hormone, a growth hormone, or a thyroid hormone.

A polyamine suitable for the invention may for example be a polylysine.

A nanoparticle suitable for the invention may for example be a metallic nanoparticle or a non-metallic nanoparticle.

According to a preferred embodiment, a targeting ligand L may be a ligand of a cellular receptor, and is preferably folic acid.

In fact, the folic acid receptor is overexpressed in many tumors such as tumors of the ovaries, breasts, kidney, brain, endometrium, colon, or in leukemia. However, it is very little, if at all, present on the surface of the healthy cells.

According to an embodiment, a targeting ligand suitable for the invention may have the form L-$(Z)_n$—, wherein n=0 or 1. Z may in particular be intended to modulate the solubility, and in particular to improve the solubility in the biological fluids, of a prodrug of the invention.

The choice of the type of the Z group is determined, on the one hand, according to the type of active compound D, the labile group E and the targeting ligand L fixed to a self-reactive arm of the invention, and, on the other hand, depending on the solubility parameters of the prodrug to be adjusted.

According to an embodiment, n may be equal to 0 or 1, and Z may be a linear or branched, saturated or insaturated, $C_1$-$C_{10}$ alkylene group, optionally interrupted by one or more heteroatoms selected from O or N, a glycosyl group, an O—$(CHR^3$—$CHR^4$—O—$)_m$, or N—$(CHR^3$—$CHR^4$—O—$)_m$ group in which m represents a natural integer varying from 1 to 20, $R^3$ and $R^4$, independently of one another, represent H or $CH_3$, provided that $R^3$ and $R^4$ do not simultaneously represent $CH_3$, a group issuing from an amino acid or a peptide, or a combination thereof.

According to an embodiment, n may be equal to 1, and Z may be a $C_1$-$C_5$, preferably $C_1$-$C_3$ alkylene group, and more preferably a methylene.

According to another embodiment, n may be equal to 1, and Z may be a glycosyl group selected from a glucosyl group, galactosyl group, marmosyl group, a lactosyl group.

According to an embodiment, Z may be a glycosyl group as defined above.

According to another embodiment, n may be equal to 1, and Z may be an O—$(CHR^3$—$CHR^4$—O—$)_m$ or N—$(CHR_3$—$CHR_4$—O—$)_m$ group in which m represents a natural integer varying between 2 and 18, preferably between 3 and 16, and more preferably between 4 and 12.

According to another embodiment, n may be equal to 1, and Z may be a group issuing from an amino acid or from a peptide. As an example of amino acids suitable for the invention, mention may be made in particular of tyrosine.

According to another embodiment, n may be equal to 1, and Z may be a combination of the groups previously defined. In particular, Z may be a combination of a glycosyl group and an O—$(CHR^3$—$CHR^4$—O—$)_m$ or N—$(CHR_3$—$CHR_4$—O—$)_m$ group as defined above.

According to another preferred embodiment, n may be equal to 0.

Preparation of a Prodrug

A compound having a general formula (II) can be prepared from a compound having the general formula (I) and from the D-v, E-w, and L-$(Z)_n$-x groups, in particular as defined below, by any method known to a person skilled in the art, In particular, a compound having the general formula (II) can be obtained by a preparation method consisting in reacting a compound having the general formula (I) or (Ia) as previously defined with D-v, E-w, and L-$(Z)_n$-x groups, wherein D, E and L and Z are as previously defined, and v, w and x each represent a reactive function such that, with regard to the compound having the general formula (I), v reacts with OH bonded to the benzyl carbon, or said previously activated OH, w reacts with X, and x reacts with F.

The reactive functions v, w and x may be naturally present on the D, E and L-$(Z)_n$ groups, or prior to the reaction step, may be introduced on the D, E and L-$(Z)_n$ groups.

It pertains to the skill of a person skilled in the art to modify the D, E and L-$(Z)_n$ groups in order to introduce therein the reactive functions v, w and x appropriate for the invention.

In particular, v, w and x are as defined below.

A method for preparing a prodrug according to the invention may comprise at least the steps consisting in reacting:

a—a compound having the general formula (I) or (Ia) with a compound E-w, b—the reaction product of step a— with a compound D-v, and c—the reaction product of step b— with a compound L-$(Z)_n$—, wherein the compounds having the general formula (I) or (Ia), E-w, D-v, and L-$(Z)_n$— are in particular as defined below.

A method of the invention may further comprise, on completion of each step a—, b— and and c—, a step of purification of the product obtained.

More particularly, the steps a—, b— and c— of a method of the invention may, in particular, be such as defined below.

According to an embodiment, a self-reactive arm according to the invention may be obtained by a method comprising at least one step consisting in chemically reacting a compound of the invention represented by the general formula (I) with a D-v group, wherein D is such as previously defined and v is a reactive function such that, with regard to the compound having the general formula (I), v reacts with OH bonded to the benzyl carbon.

According to an alternative embodiment, the chemical fixation of an active compound D to the OH function of the benzyl carbon of a compound of the invention having the general formula (I) may comprise a prior step of activation of the OH function, followed by a step of reaction of a D-v group with the activated OH function.

According to an embodiment, the OH function bonded to the benzyl carbon of a compound of the invention having the general formula (I) can be activated by reaction of said compound with a compound selected from phenyl chloroformate and derivatives thereof such as para-nitrophenyl chloroformate, dinitrophenyl chloroformate, fluorophenyl chloroformate, or carbonyl of diimidazole.

According to an embodiment, v is selected so that the chemical reaction of a D-v group with the OH function bonded to the benzyl carbon of a compound having the general formula (I), or said previously activated OH function, leads to the formation of an -A(CO)O— group bonding the group D to the benzyl carbon, wherein A may represent O, said group is a carbonate function, or A may represent NH, and said group is a carbamate function.

According to a preferred embodiment, a reactive arm of the invention is used with an OH function bonded to the previously activated benzyl carbon, as indicated above.

According to a further preferred embodiment, a D-v group is reacted with an OH function bonded to the activated benzyl carbon by reaction with a phenyl chloroformate or a derivative thereof, as indicated above.

Preferably, v is selected so that in the -A(CO)O— group A represents NH.

It pertains to the skill of a person skilled in the art to select the type of group v according to whether the chemical reaction is carried out with the OH function or an activated OH function of the benzyl carbon of a compound having the general formula (I).

When D represents a plurality of active compounds linked to an amplifier as defined above, v in the formula D-v represents the aniline or phenol function of the amplifier.

According to an embodiment, v may be selected from $NH_2$, NHR", OH, or SH, wherein R" is as previously defined. A reactive function v may be present in a functional group, for example —CONH<u>OH</u>, —CONR"<u>OH</u>, —CO<u>NH</u>$_2$, —CO <u>NH</u>R" or —N<u>H</u><u>OH</u>, wherein R" is as previously defined.

According to another preferred embodiment, the active compounds D may be coupled with the benzyl alcohol of the self-reactive arm of the invention previously activated in the form of a phenyl carbonate and derivatives thereof such as a p-nitrophenyl carbonate, a dinitrophenyl carbonate, a fluorophenyl carbonate, or a diimidazole carbonate.

According to an embodiment, a self-reactive arm according to the invention may be obtained by a method comprising at least one step consisting in chemically reacting a compound of the invention represented by the general formula (I) with an E-w group, wherein E is as previously defined and w is a reactive function such that, with regard to the compound having the general formula (I), w reacts with X.

According to an embodiment, when X represents OH, w may be a halide radical, in particular Cl or Br, and in particular Br.

According to another embodiment, when X represents $NH_2$, w may be a —COOH or —OC(O)Cl radical.

According to a particular embodiment, the enzymatically hydrolyzable labile groups E of the glycosyl group type may be introduced on a phenol function of a self-reactive arm of the invention via a chemoselective glycosylation reaction.

According to an embodiment, a self-reactive arm according to the invention may be obtained by a method comprising at least one step consisting in chemically reacting a compound of the invention represented by the general formula (I) with an L-(Z)$_n$-x group wherein L, Z and n are as previously defined and x is a reactive function such that, with regard to the compound having the general formula (I), x reacts with F by a click chemistry reaction.

The click chemistry reaction between the reactive functions F and x yields the group G having the general formula (II) defined above. The type of group G naturally depends on the type of the starting reactive functions F and x.

The click chemistry reactions and the pairs of reactive functions F and x are known to a person skilled in the art. In this respect, reference can be made to the review of Kolb et al. (Angew. Chem. Int. Ed., 2001, 40: 2004).

According to an embodiment, F is a reactive function activable by click chemistry selected from —C≡CR''', —$N_3$, —SH, —C=$CH_2$, cyclooctynes, maleimide, —$SO_2N_3$, or —COSR''' wherein R''' is H or a linear or branched, saturated or unsaturated, $C_1$ to $C_{10}$, and particularly $C_2$ to $C_6$, or even $C_3$ or $C_4$, alkyl radical.

It pertains to the skill of a person skilled in the art to select the type of group x according to the type of group F of a compound having the general formula (I).

According to an embodiment, x and F may be selected from the following pairs of reactive functions activable by click chemistry, (—$N_3$, —C≡CR'''), (—SH, —C=$CH_2$), (—$N_3$, cyclooctynes), (—SH, maleimide), (—$SO_2N_3$, —COSR'''), wherein R''' is H or a linear or branched, saturated or unsaturated, $C_1$ to $C_{10}$, and particularly $C_2$ to $C_6$, or even $C_3$ or $C_4$, alkyl radical.

According to another particular embodiment, a targeting ligand L-(Z)$_n$-x may be fixed on the group E/self-reactive arm/active compound combination by a click chemistry reaction, with an alkyne function.

In the overall application, that is to say the description presented above and the examples presented below, the expression "between . . . and . . . " relative to a range of values must be understood as including the bounds of this range.

The examples given below are presented to illustrate the subject matter of the invention and must not be interpreted as limiting its scope.

FIGURES

FIG. 1: shows the synthesis of a vector according to the invention, compound 7, by reaction on a self-reactive arm of the invention of a drug D, doxorubicin, a labile or trigger group E, galactoside, and a targeting ligand L, folate. In FIG. 1, a) is 1-bromo-(2,3,4,6-O-tetra-O-acetyl)-β-D-galactopyranoside, $Ag_2CO_3$, E1MTTA, $CH_3CN$, 84%; b) is p-nitrophenyl-chloroformate, pyridine, $CH_2Cl_2$, 92%; c) is doxorubicin, $Et_3N$, DMF, 65%; d) is NaOMe, MeOH/$CH_2Cl_2$, −15° C., 80%; e) is $CuSO_4$, sodium ascorbate, DMSO/$H_2O$, 75%.

Figure 2:
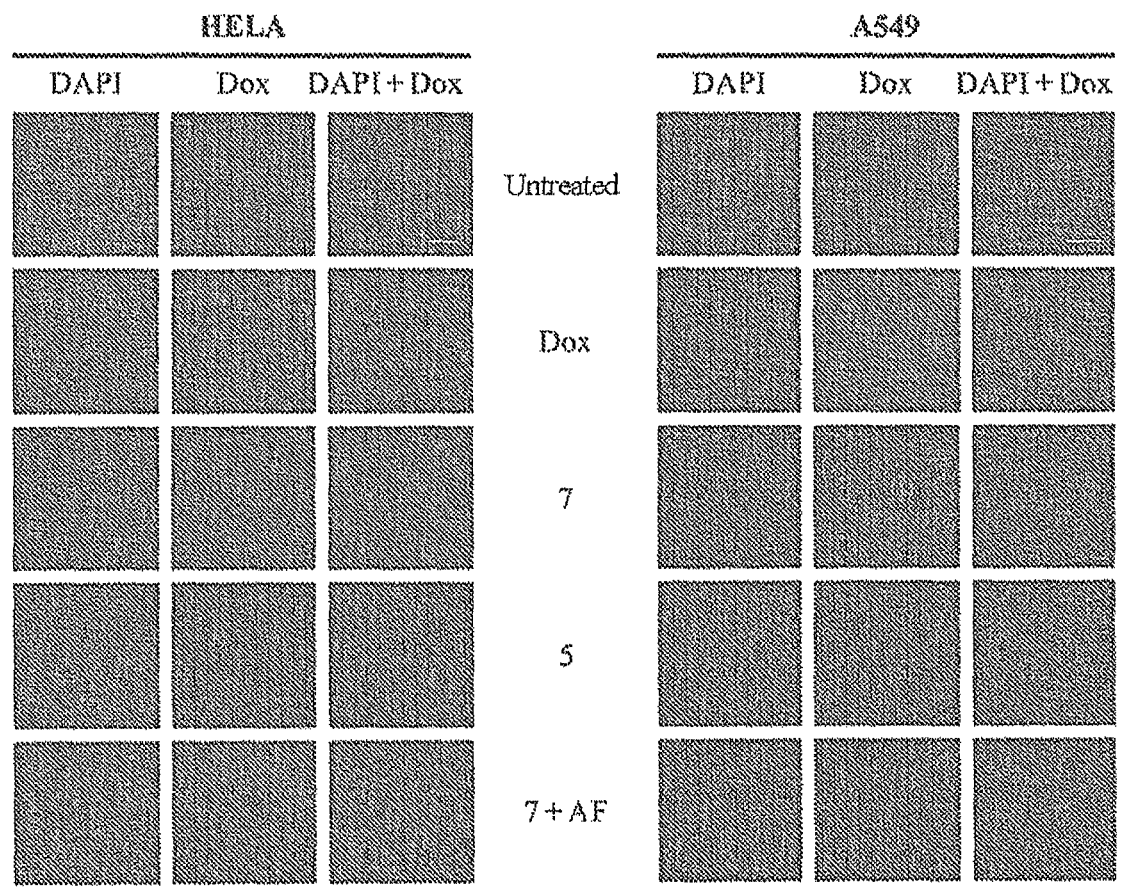

FIG. 2: shows the capacity of a prodrug of the invention (compound 7, DOX-GAL-AF) to be specifically internalized in the cells expressing a receptor for the targeting ligand (HeLa, folic acid receptor) in comparison with a compound not conforming to the invention (compound 5, DOX-GAL) and a non-vectorized active compound in the form of a prodrug (DOX), and with regard to the cells not expressing such a receptor (A549). The saturation of the cell culture medium with folic acid (+AF) prevents the entry of the compound DOX-GAL-AF into the HeLa cells.

Figure 3:
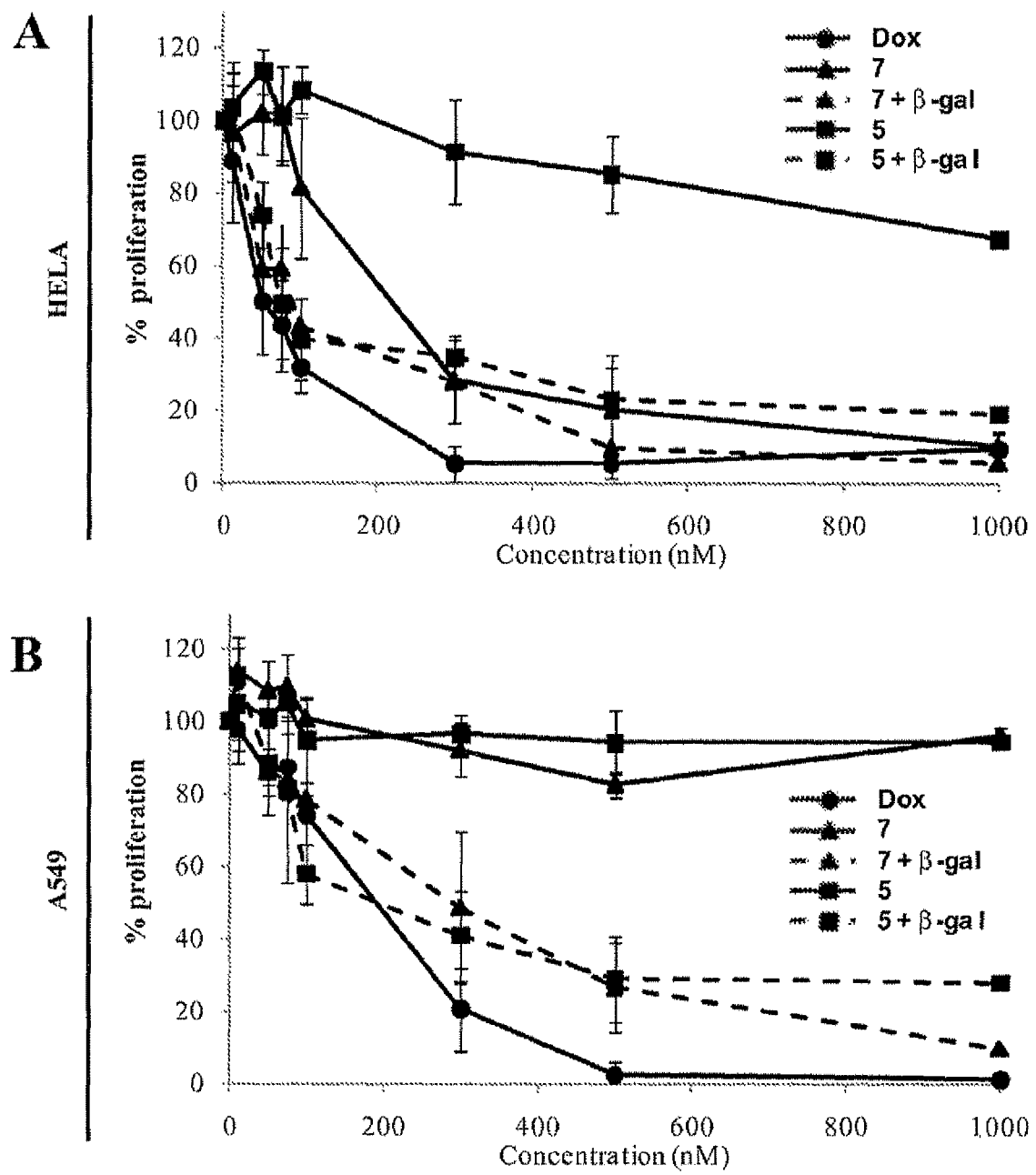

FIG. 3: shows the specific cytotoxicity of a prodrug of the invention (compound 7, DOX-GAL-AF) in a denuded culture medium (black triangle, solid line) or saturated with β-galactosidase (black triangle, dotted line), in comparison with a compound not conforming to the invention (compound 5, DOX-GAL) in a denuded culture medium (black square, solid line) or saturated with β-galactosidase (black square, dotted line), of the non-vectorized active compound in the form of a prodrug (DOX, black circle), toward cells expressing a receptor for the targeting ligand (HeLa, folic acid receptor, FIG. 3A) and cells not expressing such a receptor (A549, FIG. 3B).

Figure 4:
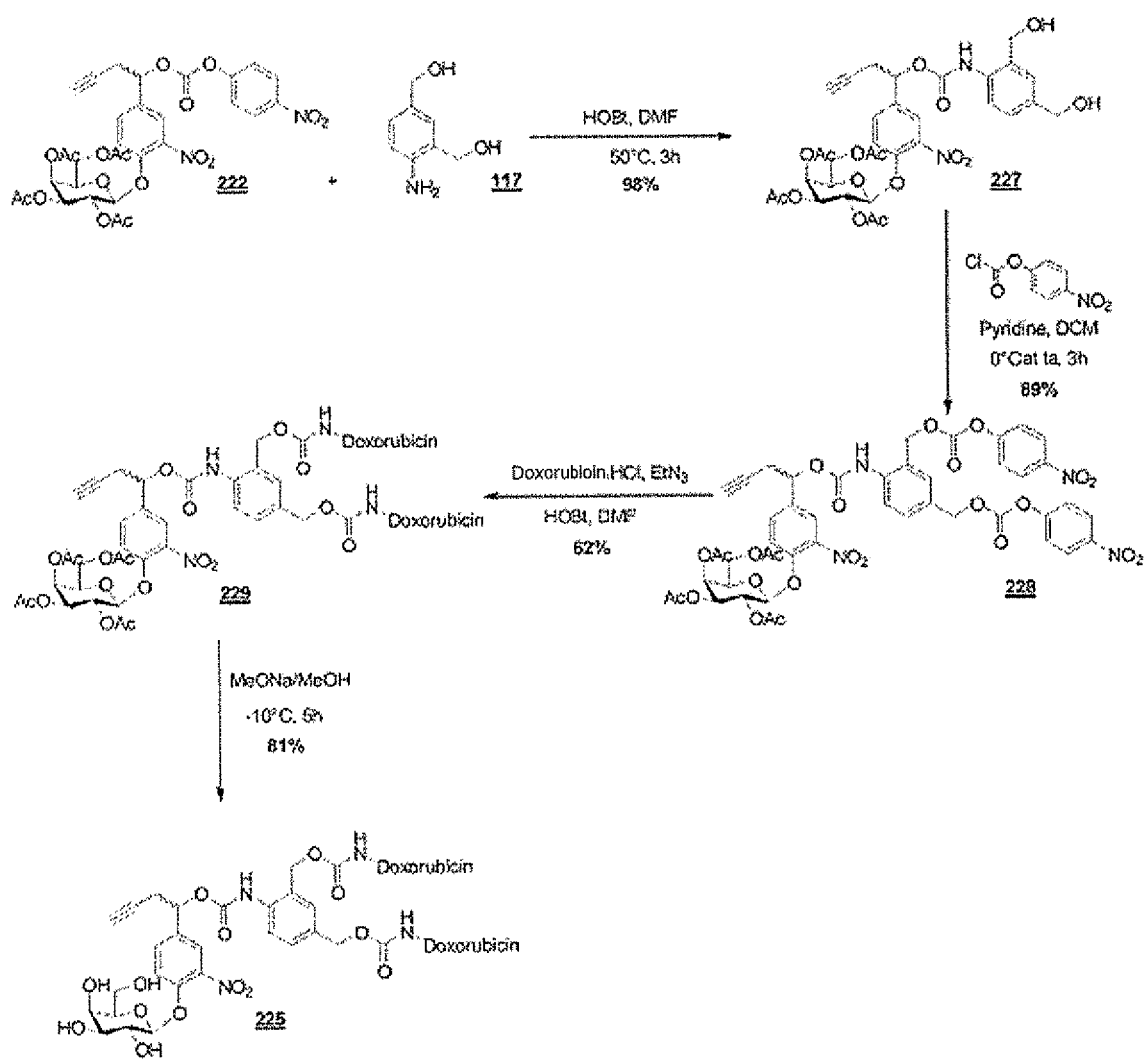
Figure 5:
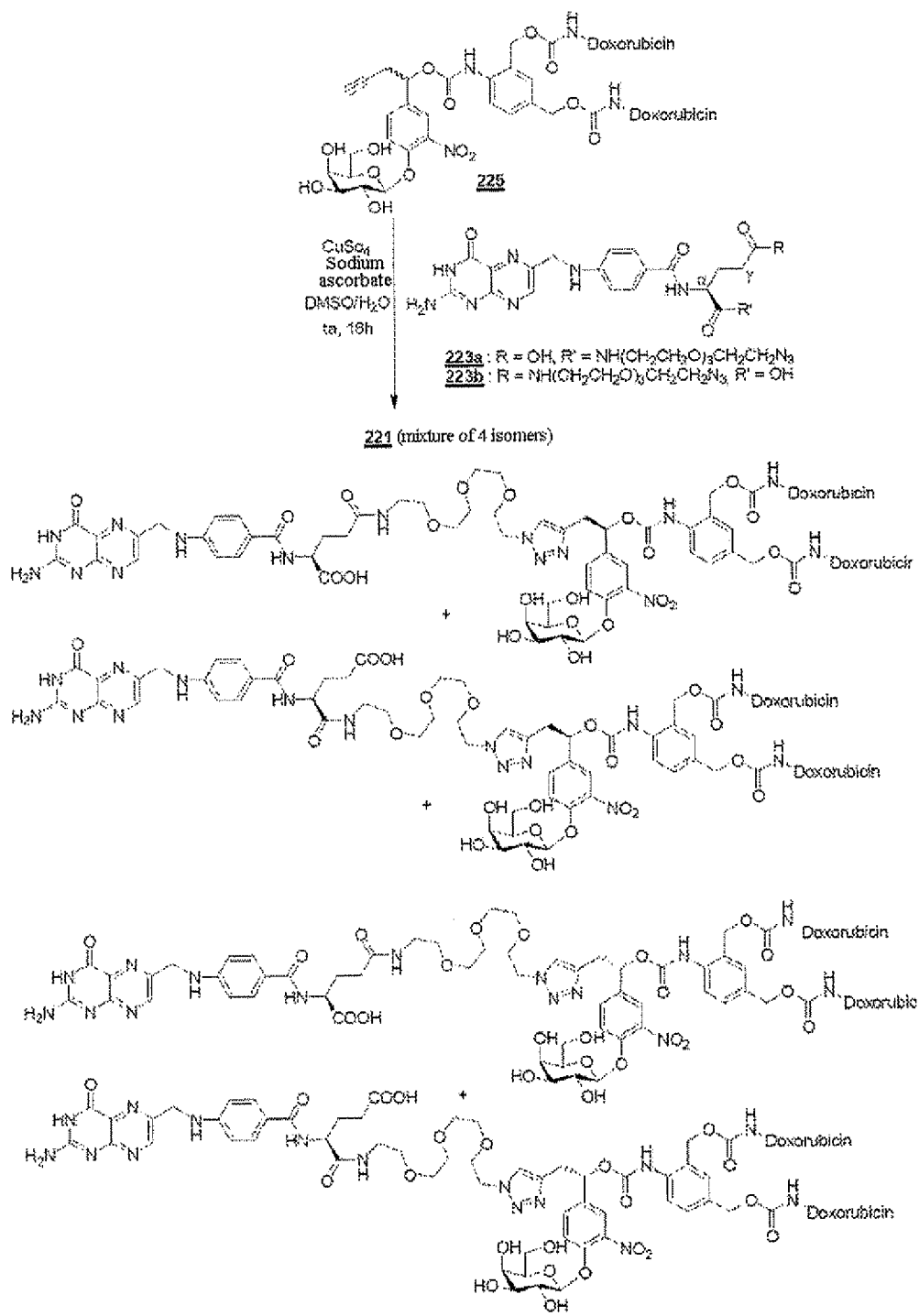

FIGS. 4 and 5: show the synthesis of a dendritic vector according to the invention, compound (221), by reaction on a self-reactive arm of the invention of a drug D consisting of a plurality of active compounds, doxorubicin, fixed to an amplifier, of a labile or trigger group E, galactosidase, and of a targeting ligand L, folate.

Figure 6:
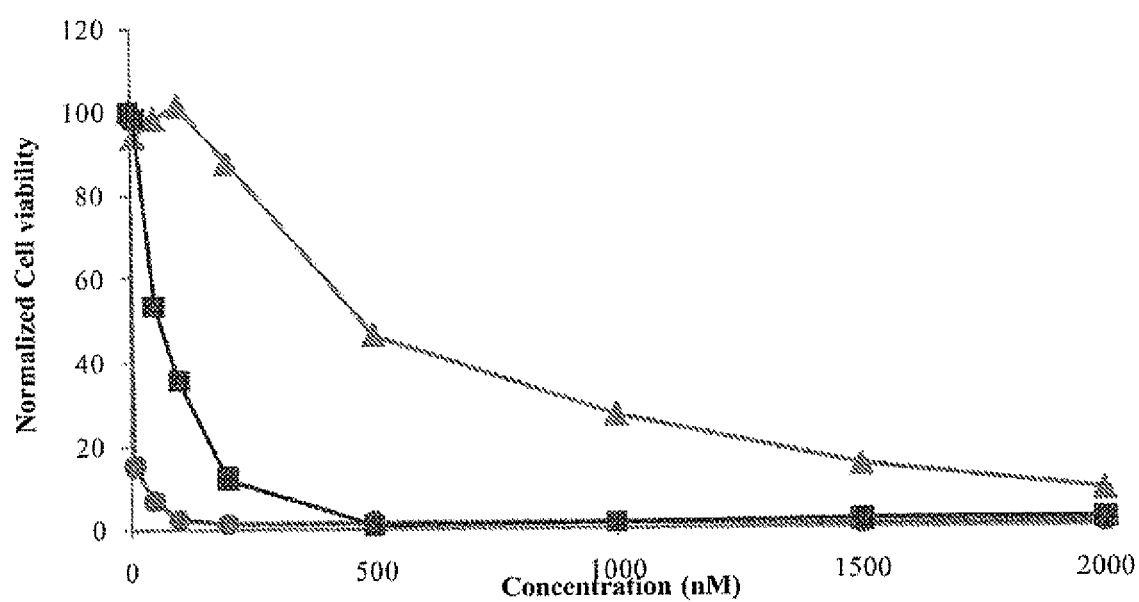

FIG. 6: shows the specific cytotoxicity of two prodrugs of the invention, compound (7), DOX-GAL-AF, (triangle) and dendritic vector (221) (square) with regard to doxorubicin (circle) on a line of cancer cells LAM type KG1.

EXAMPLES

Example 1

1—General Synthesis Method

All the reactions were carried out in nitrogen $N_2$ atmosphere. Unless otherwise indicated, the solvents used are High Performance Liquid Chromatography (HPLC) grade.

The chemical reagents used are analytical grade, obtained from commercial sources, and used without additional purification.

The progress of the reactions was monitored by thin layer chromatography (TLC) using plates precovered with a silica gel MACHEREY-NAGEL ALUGRAM® SILG/UV$_{254}$ (0.2 mm of silica gel 60). The stains were visualized after exposure of the plate to ultraviolet light (254 nm) and/or by dipping the TLC plate in a solution containing 3 g of phosphomolybdic acid in 100 ml ethanol followed by drying with a hair dryer.

The column flash chromatography was carried out using a silica gel MACHEREY-NAGEL 60 (15-40 µm) as stationary phase.

The $^1$H and $^{13}$C NMR spectra were recorded at 400 MHz on a BRUKER 400 AVANCE III instrument. The chemical shifts (δ) are reported in parts per million using tetramethylsilane as internal reference. The coupling constants (J) are reported in Hertz (Hz).

The standard abbreviations indicating a multiplicity are indicated as follows: b=broad, s=singlet, d=doublet, t=triplet, m=multiplet.

The melting points were measured on a Bachi Melting Point b-545 apparatus and not corrected.

ESI mass spectrometry was carried out by the Centre Regional des Mesures Physiques de l'Ouest (CRNPO) at the University of Rennes 1.

Analytical reverse phase HPLC (RP-HPLC) was carried out on a Dionex Ultimate 3000 device equipped with a UV/Visible variable wavelength detector and a reverse phase chromatography column ACCLAIM® (120, C18, 251×4.6 mm, 5 µm, 120 Å) at 30° C. and 1 ml·min$^{-1}$. The elution gradient was composed of A (0.2% TFA in water) and B (CH$_3$CN).

The coupled liquid chromatography mass spectrometry (LCMS) analysis was carried out with a WATERS apparatus equipped with a 3100 mass detector, a WATERS 2695 Separator module and a WATERS 2489 UV/visible variable wavelength detector. The column for reverse phase chromatography used was an ACCLAIM® (120, C18, 251×4.6 mm, 5 µm, 120 Å) column at 30° C. and 1 ml·min$^{-1}$. The elution gradient was composed of A (0.2% TFA in water) and B (CH$_3$CN).

Preparative reverse phase HPLC was carried out with a VARIAN PREPSTAR device. A solvent flow rate of 20 ml·min$^{-1}$ was applied to a VARIAN Dynamax semi-preparative column (250×21.4 mm Microsorb 100-5 C 18). The elution gradient was composed of A (0.2% TFA in water) and B (CH$_3$CN).

Method 1 (for HPLC and LCMS analysis): linear gradient starting with A/B=80/20 V/V, reaching A/B=70/30 V/V in 20 minutes and then kept constant for 20 min.

Method 2 (for preparative HPLC): linear gradient starting with A/B=80/20,V/V reaching A/B=70/30, V/V in 20 min.

2—Synthesis of Compound (7) DOX-GAL-AF

2a—Preparation of Compound (1)

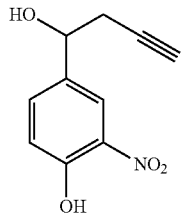
(1)

In a 250 mL three-neck round-bottom flask, 648 mg (24 mmol, 1 eq.) of aluminum and a catalytic quantity of HgCl$_2$ are covered with previously distilled THF (10 mL). 2.6 mL (24 mmol, 1 eq.) of pure propargyl bromide are added until the reaction begins (appearance of boiling in the flask and darkening of the solution). When the addition is completed, it is left at reflux for 6 hr. The solution is then cooled to 0° C. and a solution composed of 650 mg (3.84 mmol) of 4-hydroxy-3-nitrobenzaldehyde in 5 mL of distilled THF is added drop by drop. After 30 minutes of stirring, the starting product has completely disappeared, the reaction is then hydrolysed with 10 mL of HCl (1N) and then extracted three times with EtOAc. The organic phase is dried on MgSO$_4$ and then evaporated to dryness to yield a brown oil which is purified by flash chromatography (70/30, EP/EtOAc), giving a yellow oil which is diluted in 30 mL of dichloromethane. This organic phase is washed three times with NaOH (1N). The aqueous phase is acidified with concentrated HCl and extracted three times with chloroform to yield compound 1 after evaporation in the form of a brown oil with a yield of 94% (754 mg, 3.6 mmol).

Crude formula: $C_{10}H_9O_4N$ and M=207.19 g/mol $^1$H NMR (CDCl$_3$) δ (ppm): 2.05 (d, 1H, J=2.6 Hz H$_f$); 2.58 (dd, 2H, J=6.3 and 2.1 Hz, H$_e$); 3.25 (sl, 1H, OH$_{benzyl}$); 4.81 (t, 1H, J=6.2 Hz, H$_d$); 7.09 (d, 1H, J=8.7 Hz, H$_a$); 7.59 (dd, 1H, J=8.7 and 2.2 Hz, H$_b$); 8.07 (d, 1H, J=2.2 Hz, H$_c$); 10.48 (sl, 1H, O$_{phenol}$).

$^{13}$C NMR (CDCl$_3$) δ (ppm): 30.0 (C$_e$); 70.9 (C$_d$); 72.1 (C$_f$); 79.7 (C$_{alkyne}$); 120.5 (C$_{a\ or\ b}$); 122.3 (C$_{a\ or\ b}$); 132.9 (C$_{aro}$); 133.2 (C$_c$); 135.1 (C$_{aro}$); 154.6 (C$_{NO2}$).

2b—Preparation of Compound (2)

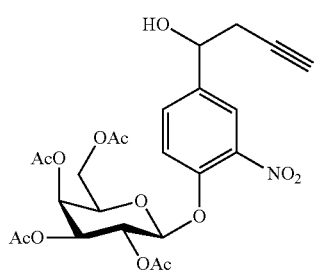
(2)

200 µL (0.7 mmol) of HMTTA and 1.0 g of Ag$_2$CO$_3$ (3.7 mmol) are placed in solution in 1.5 mL of acetonitrile. This solution is stirred for 2 hr, and 209 mg (1 mmol) of 1 and 830 mg of brominated galactose (2 mmol) are then added in succession. After 4 hr of stirring, distilled water is added, followed by extraction three times with EtOAc. The organic phases are combined and washed with an HCl solution (1N). After drying on MgSO$_4$ and evaporation to dryness, the product is purified by flash chromatography (60/40%, 50/50 and 40/60 EP/EtOAc) to give 453 mg of product 2 in the form of a yellow oil (0.84 mmol) with a yield of 84%.

Crude formula: C$_{24}$H$_{27}$O$_{13}$N and M=537.48 g/mol
F: 71° C.
$[\alpha]_D^{20}$: +42(c 0.1, CHCl$_3$)
$^1$H NMR (CDCl$_3$) δ (ppm): 2.01 (s, 3H, H$_{acetate}$); 2.03 (s, 3H, H$_{acetate}$); 2.05 (s, 4H, H$_{acetate}$ and H$_f$); 2.65 (d, 2H, J=4.2 Hz, H$_e$); 4.08-4.27 (m, 3H, H$_{5,6}$); 4.92 (t, 1H, J=5.7 Hz, H$_d$); 5.07-5.15 (m, 2H, H$_{sugar}$); 5.39-5.56 (m, 2H, H$_{sugar}$); 7.35 (d, 1H, J=8.6 Hz, H$_a$); 7.58 (t, 1H, J=8.7 Hz, H$_b$); 7.86 (d, 1H, J=8.6 Hz, H$_e$).
$^{13}$C NMR (CDCl$_3$) δ (ppm): 20.6 (C$_{acetate}$); 20.7 (C$_{acetate}$); 20.8 (C$_{acetate}$); 21.0 (C$_{acetate}$); 29.4 (C$_e$); 61.4 (C$_6$); 66.7 (C$_{sugar}$); 68.9 (C$_{sugar}$); 70.4 (C$_{sugar}$); 71.4 (C$_{sugar}$); 71.9 (C$_f$); 79.6 (C$_d$); 100.7 (C$_1$); 119.6 (C$_{CHaro}$); 122.7 (C$_{CHaro}$); 131.1 (C$_{CHaro}$); 138.8 (C$_{aro\ quaternary}$); 141.1 (C$_{aro\ quaternary}$); 148.7 (C$_{aro\ quaternary}$); 169.5 (C$_{carbonyl}$); 170.2 (C$_{carbonyl}$); 170.4 (C$_{carbonyl}$); 171.1 (C$_{carbony}$).

2c—Preparation of Compound (3)

(3)

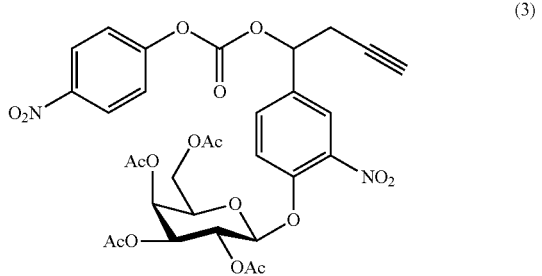

453 mg (0.84 mmol, 1 eq.) of benzyl alcohol 2 and 339 mg (1.68 mmol, 2 eq.) of para-nitrophenol chloroforrnate are placed in solution in 10 mL of DCM. The solution is cooled to 0° C., and 230 µL of pyridine (2.1 mmol, 2.5 eq.) are then added. After the complete disappearance of the starting product, distilled water is added to the medium followed by extraction three times with dichloromethane. The organic phase is dried on MgSO$_4$ and evaporated to dryness. Flash chromatography (60/40 and 50/50 EP/EtOAc) serves to isolate 384 mg of compound 3 (0.55 mmol) in the form of a yellow solid with a yield of 65%.

Crude formula: C$_{31}$H$_{30}$O$_{17}$N$_2$ and M=702.59 g/mol
F: 94° C.
$[\alpha]_D^{20}$: +32 (c 0.1, CHCl$_3$)
$^1$H NMR (CDCl$_3$) δ (ppm): 2.02 (s, 3H, H$_{acetate}$); 2.05-2.07 (s, 3H, H$_{acetate}$); 2.10 (s, 3H, H$_{acetate}$); 2.15 (s, 3H, H$_{acetate}$); 2.89 (m, 2H, H$_e$); 4.11-4.24 (m, 3H, H$_{5,6}$); 5.10 (m, 2H, H$_{sugar}$); 5.50 (m, $^2$H, H$_{sugar}$); 5.81 (t, 1H, J=5.7 Hz, H$_d$); 7.34 (d, 2H, J=7.0 Hz, H$_g$); 7.41 (d, 1H, J=8.7 Hz, H$_a$); 7.61 (dd, 1H, J=8.7 and 2.1 Hz, H$_b$); 792 (d, 1H, J=2.1 Hz, H$_e$); 8.23 (d, 2H, J=7.1 Hz, H$_h$).
$^{13}$C NMR (CDCl$_3$) δ (ppm): 25.2 (C$_{acetate}$); 25.3 (3*C$_{acetate}$); 31.0 (C$_e$); 6.9 (C$_6$); 72.8 (C$_{sugar}$); 73.5 (C$_{sugar}$); 76.0 (C$_{sugar}$); 77.1 (C$_{sugar}$); 78.1 (C$_d$); 82.73 (C$_f$); 83.9 (C$_{alkyne}$); 105.2 (C$_1$); 123.8 (C$_{CH\ aro}$); 127.8 (C$_{CH\ aro}$); 128.8 (C$_{CH\ aro}$); 130.8 (C$_{CH\ aro}$); 137.8 (C$_{CH\ aro}$); 139.0 (C$_{aro}$); 146.5 (C$_{aro}$); 151.5 (C$_{aro}$); 154.8 (C$_{aro}$); 157.1 (C$_{aro}$); 161.1 (C$_{carbonate}$); 174.2 (C$_{carbonyl}$); 174.9 (C$_{carbonyl}$); 175.2 (C$_{carbonyl}$); 175.5 (C$_{carbonyt}$)

SMHR: C$_{31}$H$_{30}$N$_2$O$_{17}$Na (M+Na)$^+$ theoretical: 725.1442. found: 725.1449.
C$_{31}$H$_{30}$N$_2$O$_{17}$K ((M+K)$^+$ theoretical: 741.1182. found: 741.1186.

2d—Preparation of Compound (4)

(4)

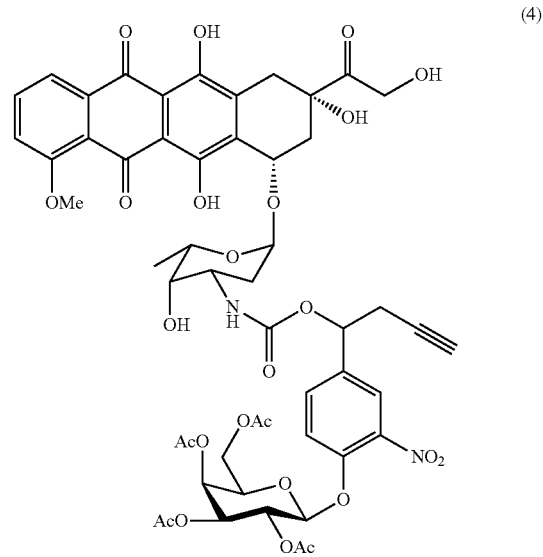

702 mg (1 mmol) of nitrophenol 3 and 580 mg (1 mmol) of doxorubicin hydrochloride are placed in solution in 15 mL of DMF. 350 µL of triethylamine (2.5 mmol) are added to the medium. The solution is stirred overnight, 25 mL of a saturated NaCl solution are then added, and the mixture is extracted three times with dichloromethane. The organic phase is dried on MgSO$_4$ and evaporated. The product is purified by flash chromatography (1.5/98.5, 3/97 and 4/96 MeOH/DCM) on silica gel. Compound 4 is isolated in the form of a red solid with a yield of 50% (554 mg, 0.50 mmol).

Crude formula: C$_{52}$H$_{54}$O$_{25}$N$_2$ and M=1107.02 g/mol
F: 172° C.
$[\alpha]_D^{20}$: +180 (c 0.1, CHCl$_3$)
$^1$H NMR (CDCl$_3$) δ (ppm): 1.25 (m, 3H, H$_{Dox\ 6}$); 1.81-2.38 and 2.68-3.23 (m, 23H); 3.47 (s, 1H); 3.58-3.83 (m, 2H); 4.07-4.21 (m, 7H); 4.51 (s, 1H); 4.74 (m, 2H); 5.25 (sl, 1H); 5.47 (m, 4H); 5.68 (m, 1H); 7.38 (d, 1H, J=8.4 Hz, H$_{aro}$); 7.48 (dd, 1H, J=8.7 and 2.1 Hz, H$_{aro}$); 7.77 (m, 2H, H$_{aro}$); 7.99 (dd, J=7.3 and 2.3 Hz, H$_{aro}$); 13.15 (d, 1H, OH$_{phenol}$); 13.92 (d, 1H, OH$_{phenol}$).
$^{13}$C NMR (CDCl$_3$) δ (ppm): 16.8; 20.6 (2*); 26.4 (2*); 31.5; 33.8; 35.6; 36.5; 47.2; 56.6; 61.3; 65.5; 66.7; 67.4; 67.8; 69.4; 69.5; 69.6; 70.5; 71.4; 71.8; 72.4; 72.5; 78.5 (2*); 100.5; 111.2; 111.4; 118.6; 119.3; 119.7; 120.6; 123.3; 131.8; 133.6; 135.3; 135.4; 135.8; 140.9; 149.1; 155.5; 156.1; 161.0; 162.7; 169.4; 170.1; 170.2; 170.3 (2*); 186.5; 186.9; 213.8.

SMHR: C$_{52}$H$_{54}$N$_2$O$_{25}$Na(M+Na)$^+$ theoretical: 1129.2913. found: 1129.2897.

$C_{52}H_{53}N_2O_{25}Na_2$ (M–2H+2Na)$^+$ theoretical: 1151.2733. found: 1151.2726.

2e—Preparation of Compound (5) DOX-GAL

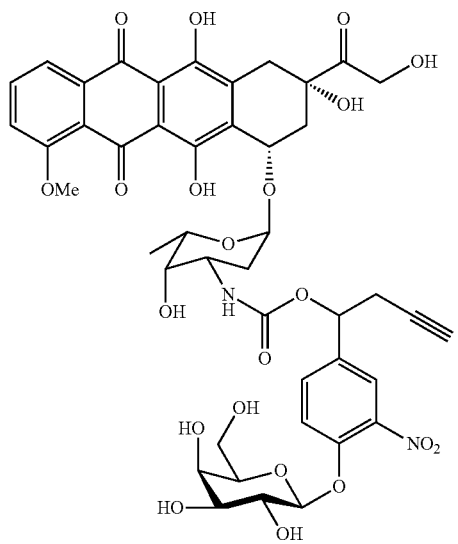

(5)

104 mg (94 µmol, 1 eq.) of prodrug 4 are diluted in 34 mL of MeOH and 6 mL of DCM. The solution is cooled to –15° C. using a cryostat. 79 mg (1.5 mmol, 16 eq.) of MeONa are added to the medium. The solution is stirred for 2 hr 15 minutes to 2 hr 30 minutes at –15° C., and then after complete disappearance of the starting product, the medium is neutralized with an acidic resin (IRC 50) for 20 minutes. The mixture is filtered on cotton, rinsed with MeOH, then evaporated to dryness. Purification by flash chromatography (6/94, 10/90 and 15/85 MeOH/DCM) serves to isolate 71 mg of product 5 (75 µmol) in the form of a red solid with a yield of 80%.

Crude formula: $C_{44}H_{48}O_{21}N_2$ and M=940.87 g/mol

F: 131° C.

$[\alpha]_D^{20}$: +128 (c 0.05, MeOH)

$^1$H NMR (MeOD) δ (ppm): 1.26 (m, 3H, H$_{6'}$); 1.82 (m, 1H, H$_{Dox\ 2'}$); 1.87-2.15 (m, 2H, H$_{Dox\ 8a/b}$ and H$_{Dox\ 2'}$); 2.25 (m, 2H, H$_f$ and H$_{8a/b}$); 2.68 (m, 3H, H$_e$ and H$_{Dox\ 10a/b}$); 2.91 (m, 1H, H$_{Dox\ 10/a\ b}$); 3.53-3.89 (m, 11H, H$_{2,3,4,5,6,3',4',OMe}$); 4.20 (m, 1H, H$_{5'}$); 4.70 (m, 2H, H$_{14}$); 4.87 (m, 1H, H$_{Dox\ 7}$); 5.0 (d, 1H, J=7.7 Hz, H$_1$); 5.33 (m, 1H, H$_1$); 5.65 (dt, 1H, H$_d$); 7.22 (d, 0.5 H, J=8.8 Hz, H$_a$); 7.31 (m, 1H, H$_{Dox\ 3}$); 7.41 (d, 0.5H, J=8.7 Hz, H$_a$); 7.50-7.63 (m, 3H, H$_{Dox\ 1,2}$ and H$_b$); 7.75 (d, 0.5H, J=1.9 Hz, H$_c$); 7.82 (d, 0.5H, J=2.0 Hz, H$_c$).

$^{13}$C NMR (MeOD) δ (ppm): 16.1; 17.2; 26.0; 29.6; 32.9; 36.1; 55.9; 61.2; 64.6; 66.4; 69.0; 70.8; 71.5; 71.8; 72.9; 73.7; 76.2; 76.8; 78.9; 98.2; 101.9; 117.6; 119.0; 119.2; 131.9; 134.4; 135.0; 136.1; 140.6; 150.0; 155.1; 155.7; 161.1; 186.3; 214.0.

SMHR: $C_{44}H_{46}N_2O_{21}Na$ (M+Na)$^+$ theoretical: 961.2491. found: 961.2497.

$C_{44}H_{45}N_2O_{21}Na_2$ (M-H+2Na)$^+$ theoretical: 983.2310. found: 983.2276.

2f—Preparation of Compound (6)

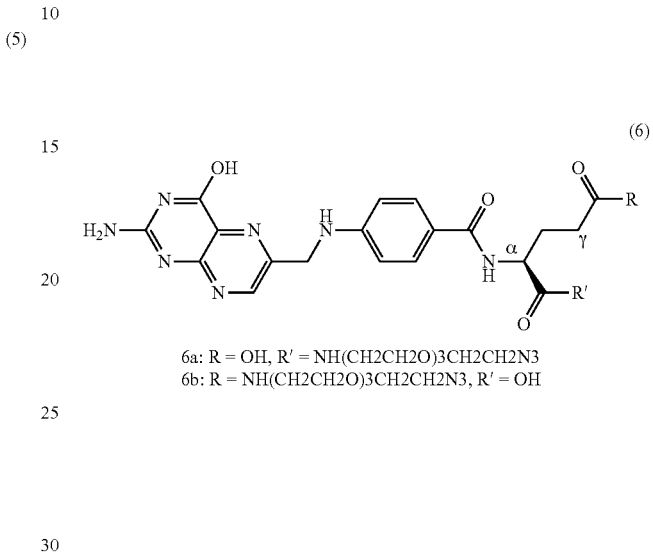

(6)

6a: R = OH, R' = NH(CH2CH2O)3CH2CH2N3
6b: R = NH(CH2CH2O)3CH2CH2N3, R' = OH 2-(2-(2-(2-Azidoethoxy)ethoxy)ethoxy)ethanamine (0.3 ml, 1.2, equiv.) (commercially available or prepared as described by Schwabacher et al., *J. Org. Chem.* 1998, 63: 1727) and dicyclohexylcarbodiimide (DCC) (650 mg, 2.5 equiv.) were added to a solution of folic acid dehydrate (600 mg, 1.26 mmol) in DMSO (20 ml) and pyridine (10 ml). The reaction mixture was stirred overnight, in darkness, at ambient temperature, giving rise to the formation of a precipitate of dicyclohexylurea (DCU). After removal of the precipitate, filtrate was poured into a solution of anhydrous ether (400 ml) cooled to 0° C. The yellow precipitate thus obtained was recovered by filtration, then washed with Et$_2$O to remove traces of DMSO. An HPLC analysis of the precipitate (Method 1) showed that the two isomers 6a and 6b were obtained in a ratio of 7/3. The solid (812 mg) was dissolved in a solution (8 ml) 8:2:0.3:0.3 H$_2$O/ACN/DMSO/Et$_3$N, and purified by reverse phase preparative HPLC (Method 2). The fraction containing the inseparable isomers 6a and 6b was concentrated under reduced pressure. The residue was then dissolved in methanol under reflux and poured into a solution of Et$_2$O cooled to 0° C. The precipitate was recovered by filtration and washed with Et$_2$O to yield a yellow powder (240 mg, 30%).

$^1$H NMR (DMSO-d$_6$) δ (ppm): 8.69 (s, 1H), 7.99 (d, 1H, J=8.3 Hz), 7.89 (t, 1H, J=5.6 Hz), 7.68 (d, 2H, J=9.7 Hz), 7.19 (bs, 1H), 6.66 (d, 2H, J=9.7 Hz), 4.53 (s, 2H), 4.4 (m, 1H), 3.72-3.19 (m, 20H), 2.30-2.20 (m, 2H), 2.11-1.82 (m, 2H)

$^{13}$C NMR (DMSO-d$_6$) δ (ppm): 174.1, 171.8, 166.7, 154.9, 153.5, 150.7, 149.2, 148.4, 129.1, 127.9, 121.2, 69.8, 69.7, 69.6, 69.5, 69.3, 68.4, 52.6, 50.0, 48.6, 45.9, 43.6, 38.5, 30.5, 27.1

SMHR: $C_{27}H_{34}N_{11}O_8$(M-H)$^-$ theoretical: 640.2593. found: 640.2586.

2g—Preparation of Compound (7) (DOX-GAL-AF)
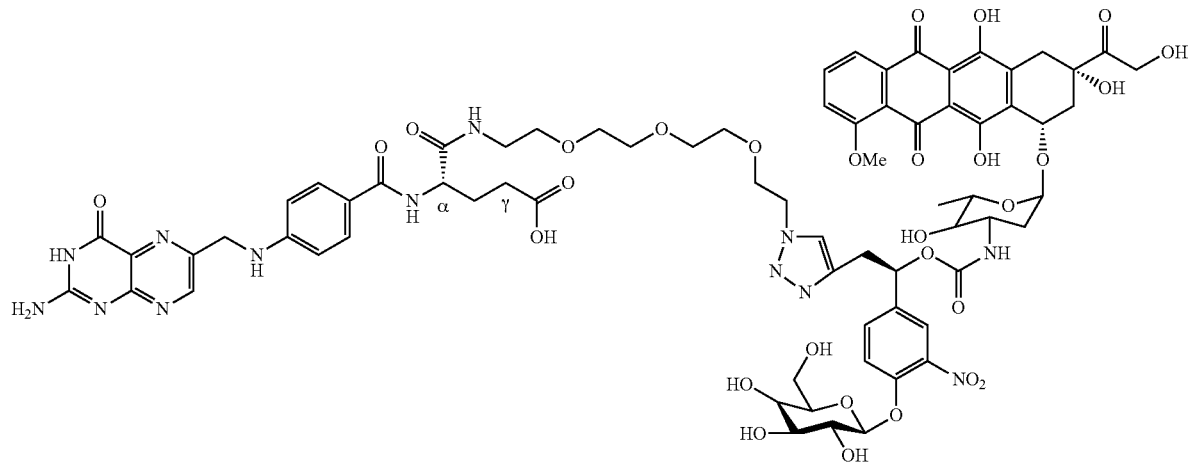
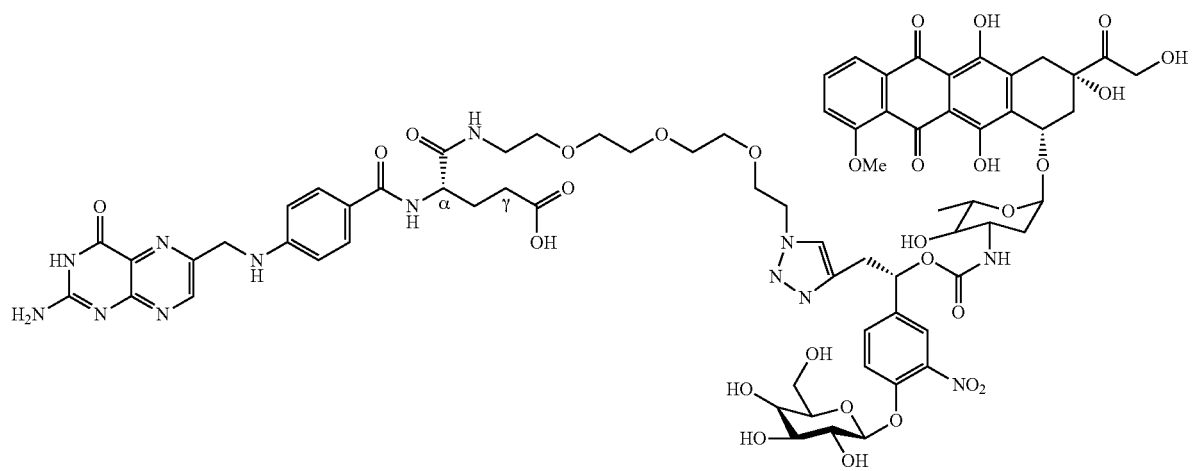
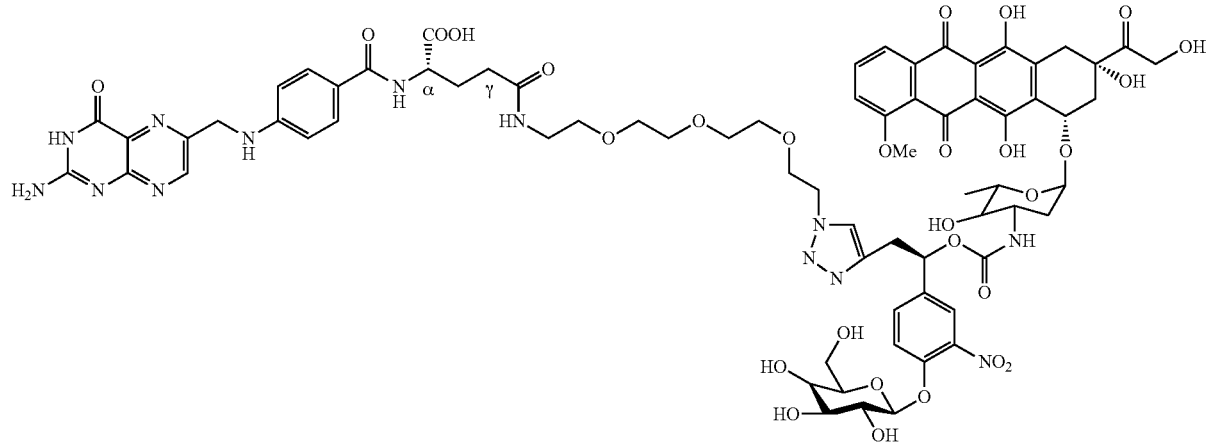

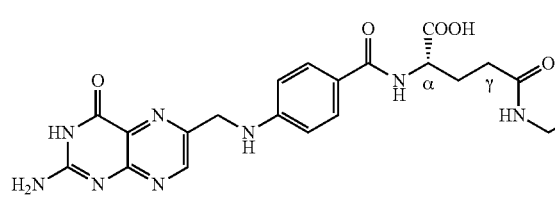
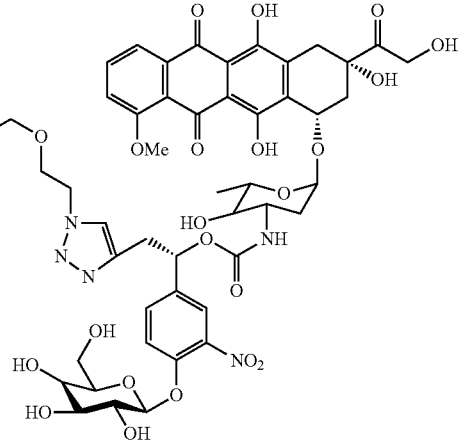

Sodium ascorbate (10.5 mg, 2 equiv.) and CuSO$_4$ (4 mg, 0.6 equiv.) were added to a solution of compound (5) (25 mg, 26 µmol) and compound (6) (16 mg, 0.95 equiv.) in DMSO (1.5 ml) containing 10% water. The solution was stirred at ambient temperature and the reaction was followed by HPLC (Method 1). Three fractions of CuSO4 (2 mg, 0.3 equiv.) were then added regularly until disappearance of compound (6). After 6 hours, the reaction mixture was diluted with MeOH (2 ml) and poured into an ether solution cooled to 0° C. The precipitate thus obtained was filtered and washed with MeOH and Et$_2$O to yield a purple colored powder (40 mg). This solid was dissolved at 0° C. in DMSO (1 ml) and a solution of EDTA. 2Na.2H$_2$O (56 mg, 6 equiv.) in phosphate buffer (1 ml, 0.2 M, pH 7). The solution was stirred at ambient temperature for 5 hours. The color then turned to red. The solution was filtered, and the filtrate was diluted with MeOH and poured into ether at 0 C. The precipitate obtained was then filtered and washed with MeOH and Et$_2$O to yield compound (7) (30 mg, 75%) in the form of a red powder. The HPLC analysis (Method 1) revealed four peaks (retention time: 23.7 min, 24.4 min, 25.3 min and 26.1 min) corresponding to the four isomers of compound (7) (DOX-GAL-AF).

$^1$H NMR (DMSO-d$_6$) δ (ppm): 8.63 (s, 1H), 7.90 (m, 5H), 7.65 (m, 4H), 7.6 (m, 2H), 7.35 (m, 2H), 6.91 (m, 2H), 6.64 (m, 2H), 5.76 (m, 1H), 5.21 (m, 1H), 4.94 (m, 3H), 4.56 (s, 3H), 4.56-4.33 (m, 7H), 4.14-3.99 (m, 7H), 2.97 (m, 3H), 2.70 (m, 1H), 2.35 (m, 1H), 2.23-2.13 (m, 4H), 2.10-1.85 (m, 4H), 1.45 (m, 1H), 1.12 (m, 3H)

SMHR: $C_{71}H_{80}N_{13}O_{29}(M-H)^-$ theoretical: 1578.51904. found: 1578.5115.

Example 2

Selectivity of Compound (7) DOX-GAL-AF

Compound (7) was tested on two cell lines, the HeLa cells, expressing the folic acid receptor (FR), and the A549 cells expressing little or none of these receptors.

The HeLa and A549 cells were cultured in RPMI 1640 medium supplemented with 10% fetal calf serum (InVitrogen) at 37° C. in an atmosphere containing 5% CO$_2$.

For confocal microscopy experiments, the cells were cultured in a glass-bottomed bowl.

The cells were incubated for 1 hour in the presence or absence of 1 µm of folic acid before being treated with either a buffer solution (control), or doxorubicin at 10 µM, or with a doxorubicin-galactose (DOX-GAL) conjugate, compound (5), in a concentration of 10 µM, or compound (7) (DOX-GAL-AF) in a concentration of 10 µM, or compound (7) in the presence of folic acid with respective concentrations of 10 µM.

After treatment, the cells were rinsed with PBS and fixed with a PBS-3.7% formaldehyde solution for 20 minutes, at room temperature.

The fixed cells were rinsed with PBS, then mounted with a Vectashield Medium in the presence of DAPI (Victor Laboratories Inc., Abcys, Paris France) before observation under the confocal microscope (FV 1000, Olympus IX-81, Tokyo, Japan). The excitation wavelengths of 405 rim and 488 nm were used respectively to acquire the images in blue (450 nm) for DAPI, and in red (590 nm) for doxorubicin.

The internalization by endocytosis of doxorobucin of the compounds (5) and (7) and of compound (7) in the presence of folic acid (AF) was monitored by confocal microscopy using the fluorescence of doxorubicin in the Hela cells and in the A549 cells.

The results obtained in this study are given in FIG. 9.

The results show that compound (7) DOX-GAL-AF is only internalized in the Hela cells, whereas doxorubicin (DOX) penetrates non-specifically through the membranes of the two cell lines, and the compound (5) DOX-GAL is not internalized in any of the cell lines.

Moreover, when the culture medium was previously saturated with folic acid, the intracellular fluorescence of doxorubicin in the Hela cells incubated in the presence of compound (7) DOX-GAL-AF is clearly attenuated.

The overall results demonstrate that compound (7) DOX-GAL-AF allows the selective and specific internalization of doxorubicin in the target cells expressing the folic acid receptor.

Example 3

Toxicity of Compound (7) DOX-GAL-AF

In order to check that the endocytosis of compound (7) DOX-GAL-AF is followed by release of the drug in the intracellular medium, proliferation tests were performed on Hela and A549 cells incubated in the presence of increasing concentrations (0 to 1000 nM) of doxorubicin (DOX), compound (5) (DOX-GAL) and compound (7) (DOX-GAL-AF) for 4 days.

The cell proliferation kit II (XTT; Roche) was used to evaluate the cellular proliferation. The kit was used following the manufacturer's recommendations.

In brief, $3 \times 10^3$ cells/well were placed on 96 culture plates and then in 100 µl of medium, The cells were cultured as previously indicated.

The cells were cultured for 24 hours before addition of the compounds tested in the indicated concentration.

After 4 days of treatment, 50 µl of XTT marking mixture were added to the well. The cells were then incubated for 4 hours at 37° C. before the absorbance was determined at 480 nm.

The results, illustrated in FIGS. 3 (A and B) show that compound (7) DOX-GAL-AF, black triangle, solid line, inhibits the proliferation of the Hela cells (0.1 µM<$IC_{50}$<0.2 µM) (FIG. 3A), whereas it has no toxicity to the A549 cells (FIG. 3B).

On the contrary, compound (5) (DOX-GAL), black square, solid line, is ineffective on the two cell lines, and doxorubicin, black circle, inhibits the proliferation of these two lines.

In order to check that the enzymatic activation of compound (7) DOX-GAF-AF can effectively take place in the cellular environment, cytotoxicity tests were repeated in a culture medium previously supplemented with β-galactosidase (E. coli) (40 U·mL$^{-1}$) (curves in dotted lines).

In this case, compound (7) exerts a similar antiproliferative activity on the two cell lines (HeLa expressing the folic acid receptor and A589 not expressing this receptor) the same antiproliferative activity.

The present invention therefore relates in particular to a novel self-reactive arm, new prodrugs comprising such an arm designed to selectively treat the target tissues. In particular, the invention relates to novel anti-cancer agents designed to selectively destroy tumors without affecting the healthy organs.

The present invention advantageously allows a therapeutic targeting or improved, and more effective diagnosis, by the use of prodrugs capable of being directed specifically to the target cells and to the microenvironment of the target cells.

More particularly, the invention relates to novel anti-cancer prodrugs capable of targeting tumor cells on the one hand, and the microenvironment of the tumor cells on the other hand.

The present invention also relates to a method for synthesizing novel prodrugs relying on a specific reactivity of the self-reactive arm of the invention. The synthesis method of the invention allows simple and effective access to a broad range of prodrugs according to the invention.

The prodrugs of the invention advantageously do not have any effect on non-targeted cells or tissues.

Example 4

Synthesis of Dendritic Vector (221)

Preparation of Compound 227

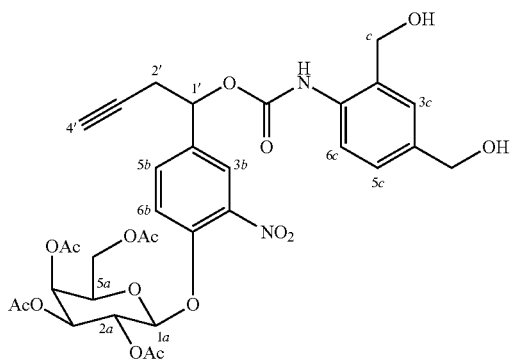 [SMILES: C#CCC(OC(=O)Nc1ccc(CO)cc1CO)c1ccc(OC2OC(COC(C)=O)C(OC(C)=O)C(OC(C)=O)C2OC(C)=O)c([N+](=O)[O-])c1]

Mixed carbonate 222 (100 mg, 0.142 mmol) and aniline 127 (43.6 mg, 0.285 mmol, 2 eq.) are diluted in 2 mL of DMF. HOBt (19.2 mg, 0.142 mmol, leg.) is added to the medium. The solution is stirred for 3 hr at 50° C. The DMF is then evaporated under vacuum. Purification by flash chromatography (50/50, 75/25 EtOAc/EP) serves to isolate the product 227 in the form of a white foam with a yield of 98% (100 mg, 0.139 mmol).

Crude formula: $C_{33}H_{36}N_2O_{16}$

M=716.62 g/mol

Rf=0.5 (EtOAc)

$^1$H NMR (400 MHz, CDCl$_3$) δ (ppm): 2.00 (s, 3H, CH$_3$COO); 2.04-2.1 (m, 7H, 2*CH$_3$COO, H$_{4'}$); 2.17 (s, 3H, CH$_3$COO); 2.65 (sl, 1H, CH$_2$OH); 2.78 (m, 2H, H$_{2'}$); 3.15 (sl, 1H, CH$_2$OH); 4.15 (m, 3H, H$_{5a}$, H$_{6a}$); 4.53 (s, 2H, H$_c$); 4.61 (s, 2H, H$_c$); 5.09 (m, 2H, H$_{3a}$, H$_{1a}$); 5.44 (d, 1H, $J_{H4a\text{-}H3a}$=3.0 Hz, H$_{4a}$); 5.51 (dd, 1H, $J_{H2a\text{-}H3a}$=11.0 Hz, $J_{H2a\text{-}H1a}$=8.0 Hz, H$_{2a}$); 5.82 (t, 1H, $J_{H1'\text{-}H2'}$=6.5 Hz, H$_{1'}$); 7.09 (d, 1H, $J_{H3c\text{-}H5c}$=1 Hz, H$_{3c}$); 7.18 (d, 1H, $J_{H5c\text{-}H6c}$=8.3 Hz, H$_{5c}$); 7.34 (d, 1H, $J_{H6b\text{-}H5b}$=8.6 Hz, H$_{6b}$); 7.58 (d, 1H, $J_{H5b\text{-}H6b}$=8.6 Hz, H$_{5b}$); 7.75 (d, 1H, $J_{H6c\text{-}H5c}$=8.3 Hz, H$_{6c}$). 7.88 (s, 1H, H$_{3b}$); 8.19 (sl, 1H, NH)

$^{13}$C NMR (100 MHz, (CD$_3$)OD) δ (ppm): 20.5-20.6 (4*OCO<u>CH$_3$</u>); 26.3-26.39 (C$_{2'}$ dia); 61.3 (C$_{6a}$); 63.9 (C$_c$); 64.4 (C$_c$); 66.7 (C$_{4a}$); 67.9 (C$_{2a}$); 70.5 (C$_{3a}$); 71.4 (C$_{5a}$); 71.9 (C$_{4'}$); 72.9 (H$_{1'}$); 78.51 (C$_{3'}$); 100.5 (C$_{1a}$); 119.4 (C$_{6b}$); 121.0 (C$_{6b}$); 123.2-123.4 (C$_{3b}$ dia); 127.5 (C$_{5c}$); 127.6 (C$_{3c}$); 129.6 (C$_{4b}$); 132.0-132.3 (C$_{5b}$ dia); 135.1 (C$_{2b}$); 136.3-136.4 (C$_{5b}$dia); 140.9 (C$_{2c}$); 141.0 (C$_{4c}$); 149.2-149.0 (C$_{1c}$ dia); 152.7 (C$_1$); 169.5470.5 (4*CO$_{acetate}$)

SMHR (ESI): $C_{33}H_{36}N_2O_{16}Na$ [M+K]$^+$ m/z theoretical: 739.19625. m/z found: 739.1961.

$C_{33}H_{36}N_2O_{16}K$ [M+K]$^+$ m/z theoretical: 755.17019. m/z found: 755.1684.

Preparation of Compound 228

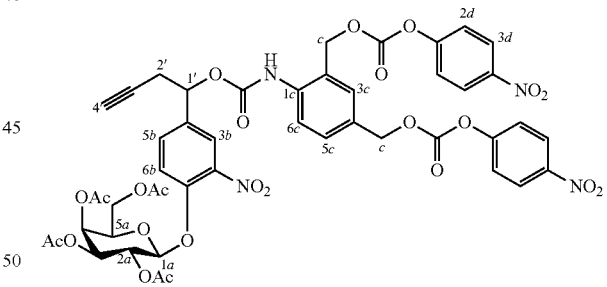

Dialcohol 227 (335 mg 0.47 mmol), in solution of 3 mL of DCM is added to a solution of para-nitrophenyl chloroformate (376 mg, 1.87 mmol, 4 eq.) and pyridine (151.3 µL, 1.87 mmol, 4 eq.) in 6 mL of DCM at 0° C. After 1 hour of stirring, the reaction mixture is hydrolyzed by a saturated NaCl solution and then extracted three times with DCM. The reaction mixture is then purified by flash chromatography (eluent: MeOH/DCM: 0/1 and 1/99) to yield compound 228 in the form of a white foam with a yield of 89% (441 mg, 0.42 mmol).

Crude formula: $C_{47}H_{42}N_4O_{24}$

M=1046.84 g/mol

Rf=0.5 (60/40: EtOAc/EP)

$^1$H NMR (400 MHz, CDCl$_3$) δ (ppm): 2.02 (s, 3H, CH$_3$COO); 2.06-2.12 (m, 7H, 2*CH$_3$COO, H$_4$); 2.19 (s, 3H, CH₃COO); 2.83 (m, 2H, HO; 4.20 (m, 3H, $H_{5a}$, $H_{6a}$); 5.12 (m, 2H, $H_{3a}$, $H_{1a}$); 5.28 (s, 2H, $H_c$); 5.34 (s, 2H, $H_c$); 5.48 (d, 1H, $J_{H4a-H3a}$=3.4 Hz, $H_{4a}$); 5.55 (dd, 1H, $J_{H2a-H3a}$=10.0 Hz, $J_{H2a-H1a}$=8.0 Hz, $H_{2a}$); 5.88 (t, 1H, $J_{H1'-H2'}$=6.5 Hz, $H_{1'}$); 7.37 (m, 5H, 5H, 4*$H_{2d}$, $H_{6b}$); 7.49 (dd, 1H, $J_{H5c-H6c}$=8.3 Hz, $J_{H5c-H3c}$=1.8 Hz, $H_{5e}$); 7.51 (d, 1H, $J_{H3c-H5c}$=1.8 Hz, $H_{3c}$); 7.59 (dd, 1H, $J_{H5b-H6b}$=8.7 Hz, $J_{H5b-H3b}$=1.6 Hz, $H_{5b}$); 7.68 (sl, 2H, NH$_{carbamate}$); 7.84 (m, 1H, $H_{6c}$); 7.91 (s, 1H, $H_{3b}$); 7.26 (m, 4H, 4*$H_{3d}$)

¹³C NMR (100 MHz, CDCl₃) δ (ppm): 20.5-20.6-20.7 (4*$C_{acetate}$); 26.3 ($C_{2'}$); 61.3 ($C_{6a}$); 66.7 ($C_{4a}$); 67.5 ($C_c$); 67.8-67.8 ($C_{2a}$ dia); 70.0 ($C_c$); 70.5 ($C_{3a}$); 71.4 ($C_{5a}$); 72.0 ($C_{4'}$); 73.3 ($C_{2a}$); 78.3-78.4 ($C_{3'}$. dia); 100.5-100.6 ($C_{1a}$ dia); 119.3-119.5 ($C_{6b}$ dia); 121.8 (4*$C_{2d}$); 123.2 ($C_{3b}$); 123.3 ($C_{6c}$); 125.3-125.4 (4*$C_{3d}$); 130.9 ($C_{5c}$); 131.7 ($C_{3c}$); 132.1-132.2 ($C_{5b}$); 134.8-134.8 (2*$C_{4d}$); 137.0 ($C_{1c}$); 141.0-141.1 (2*$C_{1d}$); 145.4 ($C_{4b}$); 145.6 ($C_{2b}$); 149.3 ($C_{4c}$); 152.4 ($C_{2c}$); 152.6 ($C_{1b}$); 152.9 (CO$_{carbamate}$); 155.1-455.4 (2* CO$_{carbonate}$); 169.3-170.1-170.2-170.3 (4*CO$_{acetate}$)

SMHR (ESI): $C_{47}H_{42}N_4O_{24}Na$ [M+N]⁺ m/z theoretical: 1069.20812. m/z found: 1069.2081.

$C_{47}H_{42}N_4O_{24}K$ [M+K]⁺ m/z theoretical: 1085.18206. m/z found: 1085.1810.

Preparation of Compound 229

Crude formula: $C_{89}H_{90}N_4O_{40}$
M=1854.51 g/mol
Rf=0.2 (7/93: MeOH/DCM)
Melting point: decomposition 215° C.

¹H NMR (400 MHz, DMSO-d6) δ (ppm): 1.19 (d, 6H, $J_{H6d-H5d}$=6.1 Hz, 2*$H_{6d}$); 1.57-1.61 (m, 2H, $H_{2d}$); 1.85-1.91 (m, 2H, $H_{2d}$); 2.01-2.27 (m, 17H, 4*CH₃COO, $H_{2'}$, $H_{4'}$, 2*$H_{ge}$); 2.88-2.98 (m, 6H, 2*$H_{10e}$, $H_{2'}$); 3.51 (m, 1H, 2*$H_{4d}$); 3.75 (m, 2H, 2*$H_{3d}$); 3.97 (2*s, 6H, 2*OMe); 4.19 (m, 4H, $H_{6a}$, 2*$H_{5d}$); 4.53 (t, 1H, $J_{H5a-H6a}$=6.1 Hz, $H_{5a}$); 4.65 (2*s, 4H, 2*$H_{14c}$); 4.74-4.79 (m, 2H, 2*$H_{7e}$, 4.92-5.09 (m, 7H, 2*$H_c$, 3*OH); 5.27-5.34 (m, 3H, $H_{2a}$, $H_{3a}$, OH); 5.42 (m, 1H, $H_{4a}$) 5.46 (sl, 1H, OH); 5.48 (sl, 1H, OH); 5.65 (d, 1H, $J_{H1a-H2a}$=7.1 Hz, $H_{1a}$); 5.84 (m, 1H, $H_{1'}$); 6.88 (d, 1H, $J_{NH-H3d}$=7.7 Hz, NH$_{carbamate}$); 6.97 (d, 1H, $J_{NH-H3d}$=7.7 Hz, NH$_{carbamate}$); 7.25 (d, 1H, $J_{H5c-H6c}$=8.4 Hz, $H_{5c}$); 7.33-7.36 (m, 2H, $H_{6b}$, $H_{3c}$); 7.45 (dd, 1H, $J_{H5b-H6b}$=8.1 Hz, $J_{H5b-H3b}$=3.4 Hz, $H_{5b}$); 7.63 (m, 2H, 2*$H_{1e}$); 7.80 (d, 1H, $J_{H6c-H5c}$$_{H5c}$=8.5 Hz, $H_{6c}$); 7.84-7.92 (m, 4H, 2*$H_{1e}$, 2*$H_{2e}$); 7.99 (s, 1H, $H_{3b}$); 9.32 (sl, 1H, NH$_{carbamate}$); 13.24 (2*s, 2H, OH$_{phenol}$); 13.97 (2*s, 2H, OH$_{phenol}$)

¹³C NMR (100 MHz, DMSO-d6) δ (ppm): 16.9 (2*$C_{6d}$); 20.2-20.3-20.4-20.5 ($C_{acetate}$); 25.4 ($C_{2'}$); 29.7 (2*$C_{2d}$); 32.1 (2*$C_{10e}$); 36.5 (2*$C_{8e}$); 47.1 (2*$C_{3d}$); 56.4-56.4 (OMe); 61.2 ($C_{6a}$); 63.6 (2*$C_{14c}$); 64.7 (2*$C_e$); 66.6 (2*$C_{5d}$); 67.0-67.6-

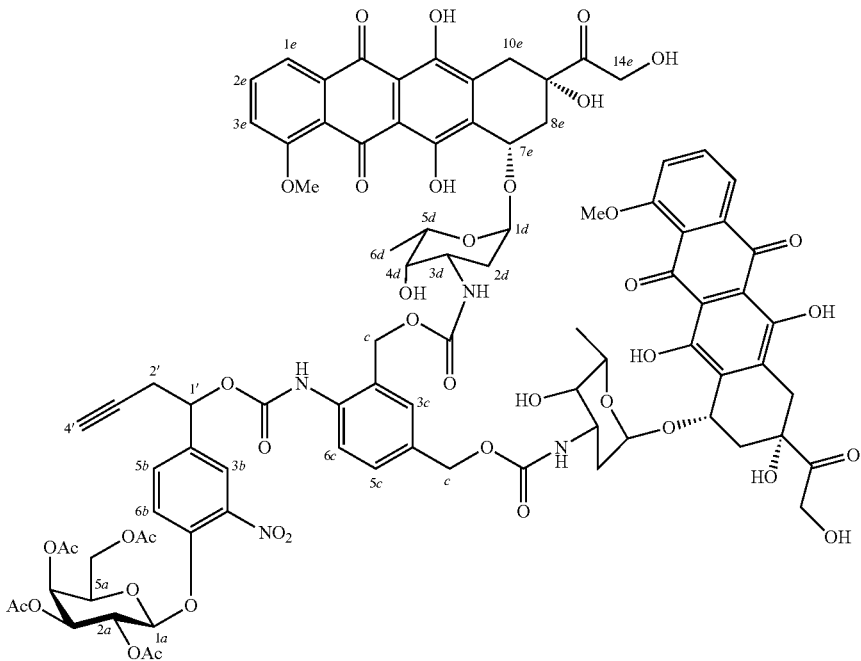

Doxorubicin hydrochloride (119.7 mg, 0.206 mmol, 2 eq.) is placed in solution in 1 mL of DMF. Triethylamine (28.7 μL, 0.206 mmol, 2 eq.) is added and the mixture is stirred at ambient temperature for 20 minutes. HOBt (27.8 mg, 0.206 mmol, 2 eq.) is then added, followed by a solution of carbonate 228 (108 mg, 0.103 mmol) in 1 mL of DMF. After 3 hours of stirring at ambient temperature, the reaction mixture is hydrolyzed by a saturated NaCl solution and then extracted 4 times with DCM and once with EtOAc. Purification by flash chromatography (0/1, 1/24: MeOH/DCM) serves to isolate product 229 in the form of a red power with a yield of 62%. (119 mg, 0.064 mmol)

67.8-69.7-69.8-70.7-73.8-74.9-75.0 (2*$C_{4d}$, $C_{2a}$, $C_{3a}$, $C_{4a}$, $C_{5a}$, 2*$C_{7e}$, $C_{1'}$, $C_{4'}$, 2*$C_{9c}$); 79.6 ($C_{3'}$); 98.4 ($C_{1a}$); 100.3 (2*$C_{1d}$); 110.4-110.6 ($C_{quaternary}$); 117.5 ($C_{6b}$); 118.8 ($C_{6c}$); 119.5-119.9 (2*$C_{3e}$); 122.5 ($C_{3b}$); 124.3 ($C_{5c}$); 127.6 ($C_{5b}$, $C_{5e}$); 130.2 ($C_{quaternary}$); 132.0 ($C_{6c}$); 133.0-134.4-134.8-135.4-135.5 ($C_{quaternary}$); 136.0 (2*$C_{2e}$, 2*$C_{1e}$); 139.9-147.9 ($C_{quaternary}$); 153.2-154.4-155.1-156.0-160.6 (3*CO$_{carbamate}$, 4*$C_{phenol}$); 168.8-169.5-169.8-169.9 (4*CO$_{acetate}$); 186.1-186.3 (4*CO$_{quinone}$); 213.7-213.8 (CO$_{ketone}$)

SMHR (ESI): $C_{89}H_{90}N_4O_{40}Na$ [M+N]⁺ m/z theoretical: 1877.5029. m/z found: 1877.5048.

Preparation of Compound 225

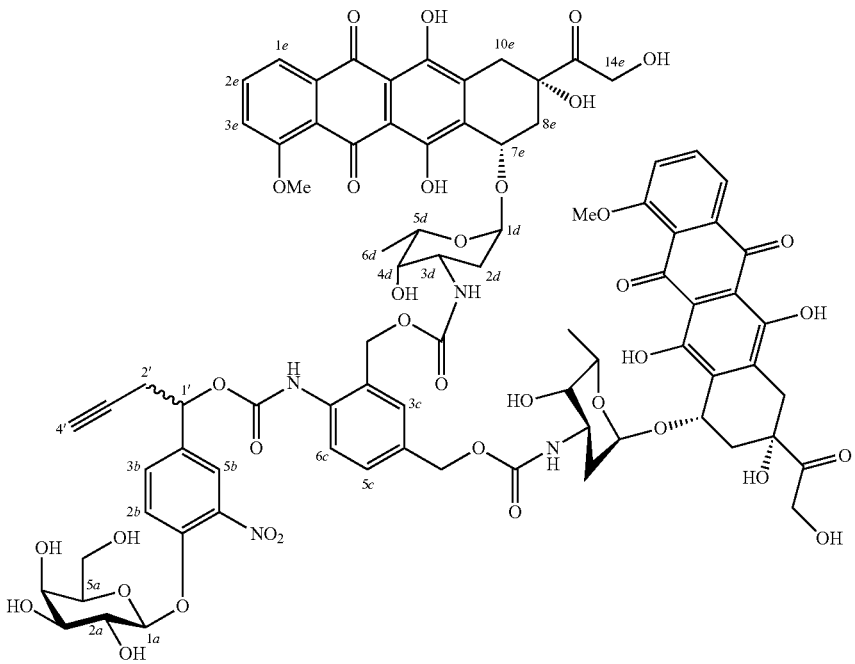

The protected compound 229 (156 mg, 84 μmol) is placed in solution in 6 mL of DCM and 10 mL of MeOH. Sodium methanolate (72.6 mg, 1.34 mmol, 16 eq.) is added with stirring at −15° C. The mixture is stirred at −10° C. for 5 hours. After complete disappearance of the starting compound, the medium is neutralized with acidic resin (IRC 50) for 15 minutes. The mixture is filtered on cotton, rinsed with MeOH, then evaporated to dryness. Purification by flash chromatography (5/95, 10/90 MeOH/DCM) serves to isolate the product 225 (115 mg, 68 μmol) in the form of a red solid with a yield of 81%.

Crude formula: $C_{81}H_{82}N_4O_{36}$
M=1686.47 g/mol
Rf=0.2 (15/85: MeOH/DCM)
Melting point: decomposition 185° C.

$^1$H NMR (400 MHz, DMSO-d6) δ (ppm): 1.11 (s, 6H, 2*$H_{6d}$); 1.22-1.87 (m, 7H, $H_2$', $H_4$', 2*$H_{2d}$); 1.98-2.21 (m, 4H, 2*$H_{8e}$); 2.81-2.96 (m, 4H, 2*$H_{10e}$); 3.37 (m, 4H, $H_{2a}$—$H_{3a}$—$H_{4a}$—$H_{5a}$, masked by HOD residual peak of solvent); 3.65 (m, 6H, 2*$H_{3d}$, 2*$H_{5d}$, 2*$H_{7e}$); 3.90 (s, 6H, 2*OMe); 4.13 (m, 3H, 2*$H_{4d}$, OH); 4.57 (m, 4H, 2$H_{14e}$); 4.70 (sl, 2H, 2*OH); 4.85-5.06 (m, 9H, 2*$CH_{2carbamate}$, $H_1$', $H_{6a}$, 2*OH); 5.14-5.32 (m, 4H, $H_{1a}$, 2*$H_{1d}$, OH), 5.40-5.54 (m, 4H, 4*OH); 6.83 (d, 1H, $J_{NH-H3d}$=8.0 Hz, $NH_{carbamate}$); 6.93 (d, 1H, $J_{NH-H3d}$=8.0 Hz, $NH_{carbamate}$); 7.20 (d, 1H, $J_{H5c-H6c}$=10.0 Hz, $H_{5c}$); 7.25 (s, 1H, $H_{3c}$); 7.35 (m, 1H, $H_{6c}$); 7.54 (d, 2H, $J_{H1e-H2e}$=8.0 Hz, 2*$H_{1e}$); 7.63 (d, 1H, $J_{H6b-H5b}$=8.0 Hz, $H_{6b}$); 7.75-7.90 (m, 6H, $H_{3b}$, $H_{6b}$, 2*$H_{2e}$, 2*$H_{3e}$); 9.08 (sl, 1H, $NH_{carbamate}$); 13.15 (s, 2H, 2*$H_{phenol}$); 13.88 (s, 2H, 2*$H_{phenol}$)

$^{13}$C NMR (100 MHz, DMSO-d6) δ (ppm): 16.9 (2*$C_{6d}$); 29.4-31.5 ($C_2$'-2*$C_{2d}$); 34.3 (2*$C_{10e}$); 36.5 (2*$C_{8e}$); 47.1 (2*$C_{3d}$); 51.9 (2*$C_{7e}$); 56.4 (2*COMe); 61.5-63.6-64.7-66.5-67.8 ($C_{6a}$, $C_1$', 2*$C_{14e}$, $C_4$'); 69.5-71.1-72.7-74.8-74.9-75.1-75.6 ($C_{2a}$, $C_{3a}$, $C_{4a}$, $C_{5a}$, $C_3$', $CH_{benzyl}$, 2*$C_{4d}$, 2*$C_{9e}$); 99.7-100.2 ($C_{1a}$-2*$C_{1d}$); 110.4-110.5 ($C_{quaternary}$); 116.8 ($C_{6b}$); 118.7-118.8-119.5-119.7 (2*$C_{1e}$-2*$C_{3e}$-$C_{quaternary}$); 124.1-124.4 ($C_{3b}$-$C_{6c}$); 127.7-128.0 ($C_{3c}$-$C_{5c}$); 130.7 ($C_{quaternary}$); 133.7-133.8-134.4-134.9436.0 ($C_{5b}$-2*$C_{2e}$-$C_{quaternary}$); 139.8 ($C_{quaternary}$); 148.6 ($C_{quaternary}$); 153.9-154.4-155.14 55.2-156.0 ($C_{quaternary}$, 3*$CO_{carbamate}$, 4*$C_{phenol}$), 186.0-186.2 (4*$CO_{quinone}$); 213.8 (2*$CO_{ketone}$)

SM (ESI): [M+Na]$^+$ m/z=1710.49
SMHR (ESI): $C_{81}H_{82}N_4O_{36}Na$ [M+Na]$^+$ m/z theoretical: 1709.4601. m/z found: 1709.4601.
$C_{81}H_{82}N_4O_{36}Na_2$ [M+2Na]$^{++}$ m/z theoretical: 866.22466. m/z found: 866.222 (z=2).

Preparation of Compound 221

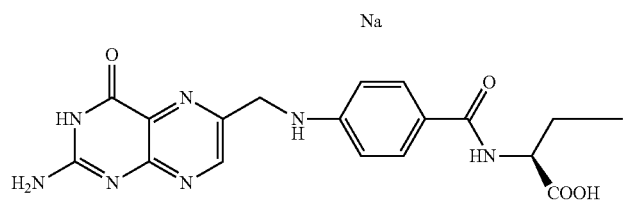

-continued

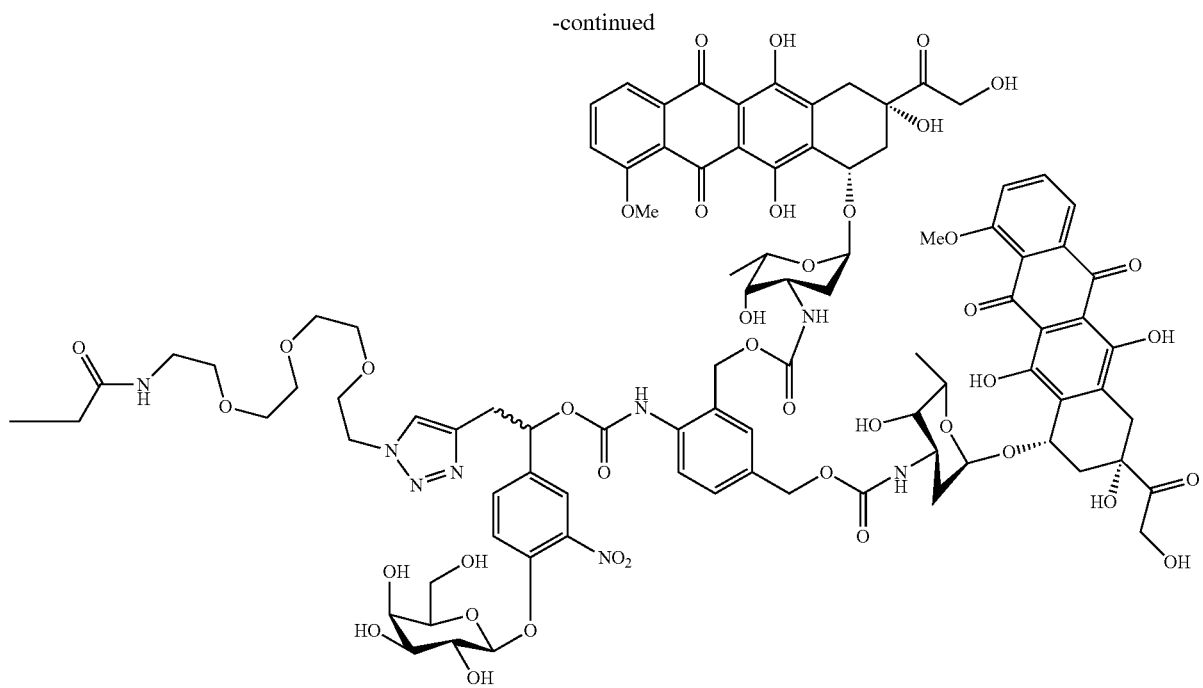

Compound 225 (30.0 mg, 17.7 μmol) is dissolved in a mixture of 700 μl of DMSO. The folate compound 223 (11.4 mg, 17.7 μmol), copper sulfate (2.2 mg, 8.9 μmol, 0.5 eq.) and 300 mL of a solution of sodium ascorbate (3.5 mg, 17.7 μmol) in a phosphate buffer pH 7 0.2M are added. After stirring overnight at ambient temperature, the reaction mixture is dissolved in methanol and then poured into cooled diethyl ether. The precipitate is filtered and then decomplexed with EDTA.2Na (41.2 mg, 4 eq.) in 1 mL of phosphate buffer pH 7 0.2M. After two hours of stirring at ambient temperature, the reaction mixture is dissolved in methanol and then poured into cooled diethyl ether. After filtration, the product 221 (11 mg, 4.7 μmol) is obtained in the form of a red powder. Purification by semi-preparative HPLC serves to obtain compound 221 in the form of 4 isomers with a purity of 89%.

Crude formula: $C_{108}H_{117}N_{15}O_{44}$

M=2327.73 g/mol

SMHR (ESI): $C_{108}H_{117}N_{15}O_{44}Na$ $[M+Na]^+$ m/z. theoretical: 2350.7277. m/z found: 2350.7279.

Example 5

Toxicity of Dendritic Vector (221)

The effectiveness of the dendritic vector (221) was compared to that of compound (7) DOX-GAL-AF and to that of Doxorubicin alone on a line of cancer cells LAM type KG-1.

$3 \times 10^3$ cells/well were placed in 96 culture plates and then in 100 μl of modified Dulbecco Iscove medium supplemented with 20% fetal calf serum (InVitrogen), and 1% penicillin/streptomycin, at 37° C. in an atmosphere containing 5% $CO_2$. The cells are cultured for 24 hours before addition of the tested compounds.

The cells are incubated in the presence of increasing concentrations (0 to 2000 nM) of doxorubicin (DOX), compound (7) (DOX-GAL-AF), and dendritic vector (221) for 4 days.

After 4 days of treatment, the viability of the cells was tested with the Cell Proliferation Kit II (XTT; Roche), used following the manufacturer's recommendations, by the addition of 50 μl of an XTT marking mixture per well. This test is based on the cleavage of the XTT by the metabolically active cells, resulting in the production of an orange formazan probe, which can be quantified by spectrophotometry.

The cells were further incubated for an additional 3 hr at 37° C. before measurement of the absorbance at 480 nm. The values of $IC_{50}$ were determined graphically.

The results, illustrated in FIG. 5, show that the dendritic vector (221) (square) reduces the viability of the LAM type KG 1 cells by a factor of about 4 to 5 more than compound (7) (triangle) (0.1 μM<$IC_{50}$<0.15 μM vs $IC_{50}$=0.5 μM) (FIG. 5), and is nearly equivalent to that of doxorubicin (circle).

The dendritic vector (221) comprises two molecules of doxorubicin for a single targeting ligand (folic acid). Compared to compound (7), this vector can lead to the release of twice the quantity of drug in the target cells or in the tumor microenvironment. Thus, thanks to the increase of the ratio [number of drugs released/number of targeting ligands] the dendritic vector (221) is more effective on cancer cells expressing the folic acid receptor. Furthermore, the increase in the ratio [number of drugs released/number of enzymatic substrates] serves to obtain a higher cytotoxic activity without changing the number of enzymatic events.

The invention claimed is:

1. A compound having a general formula (I):

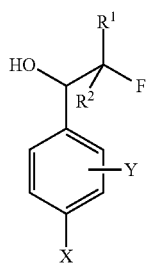

wherein:
X is OH, NH$_2$, NHOH or R'NH wherein R' is a linear or branched, saturated or unsaturated, C$_1$ to C$_{10}$ alkyl radical,
Y is an electron-withdrawing group,
R$^1$ and R$^2$, independently of one another, are H or a linear or branched, saturated or unsaturated, C$_1$ to C$_{10}$ alkyl radical,
F is a reactive function group activable by click chemistry.

2. The compound as claimed in claim 1, wherein X is OH.

3. The compound as claimed in claim 1, wherein Y is NO$_2$.

4. The compound as claimed in claim 1, wherein R$^1$ and R$^2$ are H.

5. The compound as claimed in claim 1, wherein F is —C≡CR''', —N$_3$, —SH, —C═CH$_2$, cyclooctynes, maleimide, —SO$_2$N$_3$, or —COSR''', wherein R''' is H or a linear or branched, saturated or unsaturated, C$_1$ to C$_{10}$ alkyl radical.

6. A compound having a general formula (II):

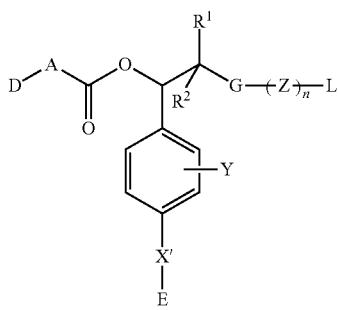

wherein:
R$^1$ and R$^2$ are as claimed in claim 1,
Y is an electron-withdrawing group,
X' is O, NH, NOH, R'N wherein R' is as claimed in claim 1,
E is a labile group linked to X' by a carboxyl group or an ether bond,
A is O, S, NH, NR'' wherein R'' is a linear or branched, saturated or unsaturated, C$_1$ to C$_{10}$ alkyl group,
D is an active compound usable in therapy or diagnosis,
n=0 or 1, and Z is a linear or branched, saturated or unsaturated, C$_1$-C$_{10}$ alkylene group optionally interrupted by one or more heteroatoms selected from the group consisting of O or N, a glycosyl group, an O—(CHR$^3$—CHR$^4$—O—)$_m$ or N—(CHR$^3$—CHR$^4$—O—)$_m$ group in which m is a natural integer varying from 1 to 20, R$^3$ and R$^4$, independently of one another, are H or CH$_3$, provided that R$^3$ and R$^4$ are not simultaneously CH$_3$, a group coming from an amino acid or from a peptide, and a combination thereof,
L is a targeting ligand selected from the group consisting of a peptide, a protein, an antibody or an antibody fragment recognizing an antigen, a ligand of a cellular receptor, a biopolymer, a monosaccharide, an oligosaccharide, a hormone, a vitamin, a dendrimer, a polyamine, and a nanoparticle,
G is a group resulting from a click chemistry reaction between an F group, as claimed in claim 1, and an x-(Z)n-L group wherein Z and L are as claimed above and x is a reactive function group activable by click chemistry and capable of reacting with F, or a pharmaceutically acceptable salt thereof.

7. The compound as claimed in claim 6, wherein Y is NO$_2$ in the ortho position of X', and R$^1$ and R$^2$ are H.

8. The compound as claimed claim 6, wherein D is a compound having therapeutic activity.

9. The compound as claimed in claim 6, wherein D comprises an active compound or a plurality of active compounds.

10. The compound as claimed in claim 6, wherein the labile group E is a substrate of glucuronidases.

11. The compound as claimed in claim 6, wherein L is a ligand of a cellular receptor.

12. The compound as claimed in claim 6, wherein n=1 and Z is a C$_1$-C$_5$ alkylene group.

13. The compound as claimed in claim 6, wherein n=1 and Z is a glycosyl group selected from the group consisting of a glucosyl group, a galactosyl group, a malmosyl group, and a lactosyl group.

14. The compound as claimed in claim 6, wherein n=1 and Z is a O—(CHR$^3$—CHR$^4$—O—)$_m$ or N—(CHR$^3$—CHR$^4$—O—)$_m$ group wherein in is a natural integer varying from 2 to 18.

15. The compound as claimed in claim 6, wherein n=1 and Z is a group coming from an amino acid or from a peptide.

16. The compound as claimed in claim 6, wherein n=1 and Z is a combination of a glycosyl group and a O—(CHR$^3$—CHR$^4$—O—)$_m$ or N—(CHR$_3$—CHR$_4$—O—)$_m$ group.

17. The compound as claimed in claim 6, wherein n=0.

18. A method for preparing a compound as claimed in claim 6, comprising providing a compound having the general formula (I):

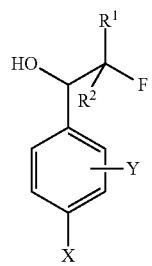

wherein:
X is OH, NH$_2$, NHOH or R'NH wherein R' is a linear or branched, saturated or unsaturated, C$_1$ to C$_{10}$ alkyl radical,
Y is an electron-withdrawing group,
R$^1$ and R$^2$ are H or a linear or branched, saturated or unsaturated, C$_1$ to C$_{10}$ alkyl radical,
F is a reactive function group activable by click chemistry,
to react with D-v, E-w, and L-(Z)$_n$-x groups, wherein D, E and L and Z are as claimed in claim 6, and v, w and x are each a reactive function group such that, with regard to the compound having the general formula (I), v reacts with OH linked to the benzyl carbon, or said previously activated OH, w reacts with X, and x reacts with F.

19. The method as claimed in claim 18, wherein v is selected from the group consisting of NH$_2$, NHR'', OH, and SH.

20. The method as claimed in claim 18, wherein w is a halide radical.

21. The method as claimed in claim 18 wherein x and F are selected from the group consisting of following pairs of reactive function groups activable by click chemistry, (—$N_3$, —C≡CR'''), (—SH, —C=$CH_2$), (—$N_3$, cyclooctynes), (—SH, maleimide), and (—$SO_2N_3$, —COSR'''), wherein R''' is H or a linear or branched, saturated or unsaturated, $C_1$ to $C_{10}$ alkyl radical.

22. A compound or a pharmaceutically acceptable salt thereof, obtainable by the method as claimed in claim 18.

23. A pharmaceutical or diagnostic composition comprising at least an effective quantity of at least one compound having the general formula (II) as claimed in claim 6, or a pharmaceutically acceptable salt thereof.

24. The pharmaceutical composition as claimed in claim 23, wherein the compound has the general formula (II), or a pharmaceutically acceptable salt thereof, wherein the active compound D is an active anti-cancer compound, and the composition is intended for a prevention and/or treatment of a cancer.

25. A kit for preparing a compound having the general formula (II) as claimed in claim 6, or a pharmaceutically acceptable salt thereof, comprising at least one compound having the general formula (I):

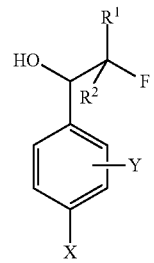

wherein:
X is OH, $NH_2$, NHOH or R'NH wherein R' is a linear or branched, saturated or unsaturated, $C_1$ to $C_{10}$ alkyl radical,
Y is an electron-withdrawing group,
$R^1$ and $R^2$ are H or a linear or branched, saturated or unsaturated, $C_1$ to $C_{10}$ alkyl radical,
F is a reactive function group activable by click chemistry,
and at least one selected from the group consisting of D-v, E-w, and L-$(Z)_n$-x, wherein L, Z, n, D and E are as claimed in claim 6, and v, w and x are each a reactive function group such that with regard to the compound having the general formula (I) and the D-v, E-w, and L-(Z)n-x being conditioned separately.

26. The compound as claimed in claim 1, wherein Y is $NO_2$, $CF_3$, or a halogen group.

* * * * *